United States Patent [19]

Hsu et al.

[11] Patent Number: 5,354,762
[45] Date of Patent: Oct. 11, 1994

[54] SIX-MEMBERED HETEROCYCLIC DERIVATIVES OF N′-SUBSTITUTED-N,N′-DIACYLHYDRAZINES

[75] Inventors: Adam C. Hsu, Lansdale; Dat P. Le, North Wales, both of Pa.

[73] Assignee: Rohm and Haas Company, Philadelphia, Pa.

[21] Appl. No.: 12,380

[22] Filed: Feb. 19, 1987

Related U.S. Application Data

[63] Continuation-in-part of Ser. No. 885,508, Jul. 14, 1986, abandoned.

[51] Int. Cl.$^5$ ............... A61K 31/16; A61K 31/17; C07D 211/72; C07D 211/84
[52] U.S. Cl. ............................ 514/338; 514/346; 514/353; 514/357; 546/291; 546/270; 546/305; 546/306; 546/316; 546/324; 546/331; 546/332
[58] Field of Search .............. 546/291, 305, 306, 316, 546/324, 331, 332, 270; 514/346, 353, 357, 338

[56] References Cited

U.S. PATENT DOCUMENTS

| | | |
|---|---|---|
| 2,758,054 | 8/1956 | Smith et al. ............... 546/291 |
| 3,092,660 | 6/1963 | Gutmann et al. .......... 546/291 |
| 3,636,112 | 1/1972 | Draber et al. ............. 546/291 |
| 3,699,111 | 10/1972 | Kaugars ..................... 546/291 |
| 3,737,533 | 6/1973 | Moon et al. ............... 546/291 |
| 3,745,215 | 7/1973 | Kaugars ..................... 546/291 |
| 3,746,760 | 7/1973 | Sheppard et al. .......... 546/291 |
| 3,748,356 | 7/1973 | Wellinga et al. ........... 546/291 |
| 3,786,094 | 1/1974 | Perronnet et al. ......... 546/291 |
| 3,809,703 | 5/1974 | Kaugars ..................... 546/291 |
| 3,821,261 | 6/1974 | Kaugars ..................... 546/291 |
| 3,824,233 | 7/1974 | Friedman ................... 546/291 |
| 3,834,892 | 9/1974 | Moon et al. ............... 546/291 |
| 3,867,449 | 2/1975 | Moore ........................ 546/291 |
| 3,870,505 | 3/1975 | Kaugars ..................... 546/291 |
| 3,879,542 | 4/1975 | Kaugars ..................... 546/291 |
| 3,897,559 | 7/1975 | Friedman ................... 546/291 |
| 3,932,660 | 1/1976 | Moore ........................ 546/291 |
| 3,989,842 | 11/1976 | Wellinga et al. ........... 546/291 |
| 4,007,165 | 2/1977 | MacLeay et al. ........... 546/291 |
| 4,008,217 | 2/1977 | Moon et al. ............... 546/291 |
| 4,008,273 | 2/1977 | MacLeay et al. ........... 546/291 |
| 4,017,540 | 4/1977 | Kaugars et al. ............ 546/291 |
| 4,018,645 | 4/1977 | Takahashi et al. ......... 546/291 |
| 4,062,934 | 12/1977 | Tilly et al. ................. 546/291 |
| 4,198,434 | 4/1980 | Bergman et al. ........... 546/291 |
| 4,203,932 | 5/1980 | Brown ........................ 546/291 |
| 4,258,059 | 3/1981 | Auerbach et al. .......... 546/291 |
| 4,268,511 | 5/1981 | Baronnet et al. ........... 546/291 |
| 4,508,734 | 4/1985 | Lang et al. ................. 546/291 |
| 4,533,676 | 8/1985 | Sirrenberg et al. ......... 546/291 |
| 4,547,524 | 10/1985 | Kaneko et al. ............. 546/291 |
| 4,550,204 | 10/1985 | Von Gentzkew et al. .. 546/291 |
| 4,551,472 | 11/1985 | D'Silva ...................... 546/291 |
| 4,564,611 | 1/1986 | Stahler et al. .............. 546/291 |

FOREIGN PATENT DOCUMENTS

| | | |
|---|---|---|
| 8508303 | 4/1985 | European Pat. Off. ........ 546/291 |
| 1668893 | 10/1971 | Fed. Rep. of Germany ... 546/291 |
| 2757584 | 8/1978 | Fed. Rep. of Germany ... 546/291 |
| 8005 | 7/1970 | France ........................... 546/270 |
| 1481388 | 7/1977 | United Kingdom ............ 546/291 |
| 1573668 | 8/1980 | United Kingdom ............ 546/291 |

OTHER PUBLICATIONS

25 Aust. J. Chem., 523–529 (1972).
61 Helv. Chim. Acta, 1477–1510 (1978).
44 J.A.C.S., 2556–2567 (1922).
44 J.A.C.S., 1557–1764 (1922).
48 J.A.C.S., 1030–1035 (1926).
27 Bull. Chem. Soc. Japan, 624–627 (1957).
51 Can. J. Chem., 1587–1597 (1973).
20 J. Agr. Food Chem., 1187–1190 (1972).
Chem. Abstracts, 77: 34128c (1972).

(List continued on next page.)

Primary Examiner—Johann Richter
Attorney, Agent, or Firm—Terence P. Strobaugh

[57] ABSTRACT

This invention relates to insecticidal compositions containing six-membered heterocyclic derivatives of N′-substituted-N,N′-diacylhydrazines, methods of using such compositions and novel six-membered heterocyclic derivatives of N′-substituted-N,N′-diacylhydrazines.

78 Claims, No Drawings

OTHER PUBLICATIONS

28 Aust. J. Chem., 133–141 (1975).
88 J.A.C.S., 4677–4681 (1966).
Bentley, T. et al, "Aspects of Mass Spectra of Organic Compounds. Part XI. Rearrangements in Benzoylhydrazines", J. Chem. Soc., Perkin I, 449–453 (1973).
40 J. Org. Chem., 19–24 (1975).
44 J. Org. Chem., 2957–2961 (1979).
46 J. Org. Chem., 83–89 (1980).
J. Chem. Soc. Perkin II, 382–390 (1978).
Chem. Abstracts, 79:122571p (1973).
Chem. Abstracts, 77:126648a (1972).
13 Aldrichimaca Acta., 37–40 (1980).
8 J. Pharm. Sci. U.A.R., 181–186 (1967).
23 J. Agric. Food Chem., 1084–1088 (1975).
48 J. Org. Chyem., 2287–2289 (1983).
92 Bull. Soc. Chim. Belg., 229–232 (1983).
48 Canadian J. of Chem., 81–88 (1970).
24 J. Med. Chem., 532–538 (1981).
Friedman et al, "The Photolysis of Benzoyl Chloride (2,4,6-Trichloro-Phenyl)Hydrazone," Pest. Chem., Proc. Int. IUPAC Cangs. Pest Chem., 3rd. 298–301 (1970).
Chem. Abstracts 93:94943e (1980).
Chem. Abstracts 73:3623y (1970).
Chem. Abstracts 96:99275k (1982).
Chem. Abstracts 765:8814a (1966).
36, J. Prakt. Chem., 197–201 (1967).
26 J.O.C., 4336–4340 (1961).
41 J.O.C., 3763–3765 (1976).
94 J.A.C.S., 7406–7416 (1972).
43 J.O.C., 808–815 (1978).
39 J. Econ. Ent., 416–417 (1946).
20 J. Agr. Food Chem., 888–891 (1972).
21 J. Agr. Food Chem., 647–650 (1973).
J. Chem. Soc.(c), 1531–1536 (1966).
J. Chem. Soc., 4191–4198 (1952).
56 B Chem. Berichte, 954–962 (1923).
32 Zhur. Obs. Khim., 2806–2809 (1962).
590 Annalen der Chemie, 1–36 (1954).
17 Acta. Chim. Scand., 95–102 (1963).
25 Zhur. Obs. Khim, 1719–1723 (1955).
J. Chem. Soc., 4793–4800 (1964).
57 *J. Pharm. Sci.*, 2011–2012 (1968).
*Chemical Abstracts,* 95:132148a (1981).
*Chemical Abstracts,* 85:142768k (1976).
*Chemical Abstracts,* 82:39589s (1975).

SIX-MEMBERED HETEROCYCLIC DERIVATIVES OF N'-SUBSTITUTED-N,N'-DIACYLHYDRAZINES

This application is a continuation-in-part of Ser. No. 06/885,508 filed Jul. 14, 1986, now abandoned.

BACKGROUND OF THE INVENTION

This invention relates to six-membered heterocyclic derivatives of N'-substituted-N,N'-diacylhydrazines which are useful as insecticides, compositions containing those compounds and methods of their use. Certain of the disclosed hydrazines are new compounds.

The search for compounds which have a combination of excellent insecticidal activity and low undesirable toxicity is a continuing one because of factors such as the desire for compounds exhibiting greater activity, better selectivity, low undesirable environmental impact, low production cost and effectiveness against insects resistant to many known insecticides.

Compounds of the present invention are particularly suitable for controlling plant-destructive insects in crops of cultivated plants, ornamentals and forestry.

Certain hydrazine derivatives have been disclosed in the literature.

In 25 *Aust. J. Chem.*, 523–529 (1972), several N,N'-dibenzoylhydrazine derivatives are disclosed including N'-i-propyl-; N'-n-propyl-; N'-(2-methylpropyl)-; N'-(3-methylbutyl)-; N'-benzyl- and N'-phenyl-N,N'-dibenzoylhydrazine in which one or both nitrogen atoms are alkylated or phenylated. No biological activity is disclosed for those compounds.

In 61 *Helv. Chim. Acta*, 1477–1 510 (1978), several N,N'-dibenzoylhydrazine and hydrazide derivatives including N'-t-butyl-N-benzoyl-N'-(4-nitrobenzoyl)hydrazine are disclosed. No biological activity is disclosed for those compounds.

In 44 *J.A.C.S.*, 2556–2567 (1922), isopropylhydrazine $(CH_3)_2CH-NH-NH_2$, symmetrical diisopropylhydrazine, dibenzoylisopropylhydrazine and certain derivatives are disclosed. No biological activity is disclosed for those compounds.

In 44 *J.A.C.S.*, 1557–1564 (1972), isopropyl, menthyl and bornyl semicarbazides are disclosed. No biological activity is disclosed for those compounds.

In 48 *J.A.C.S.*, 1030–1035 (1926), symmetrical dimethylphenylmethylhydrazine and certain related compounds including 1,2-bis-methylphenylmethyl-4-phenyl-semicarbazide are disclosed. No biological activity; is disclosed for those compounds.

In 27 *Bull. Chem. Soc. Japan*, 624–627 (1954), certain hydrazine derivatives including alpha,betadibenzoylphenylhydrazine are disclosed. No biological activity is disclosed for those compounds.

In *J. Chem. Soc.* (C), 1531–1536 (1966), N,N'-dibenzoylphenylhydrazine and N-acetyl-N'-benzoyl-p-nitrophenylhydrazine are disclosed. No biological activity is disclosed for those compounds.

In 56B *Chem. Berichte*, 954–962 (1923), symmetrical di-isopropylhydrazines, symmetrical diisobutyl- and certain derivatives including N,N'-diisobutyldibenzoylhydrazine are disclosed. No biological activity is disclosed for those compounds.

In 590 *Annalen der Chernie*, 1–36 (1954), certain N,N'-dibenzoylhydrazine derivatives are disclosed including N'-methyl- and N'-(2-phenyl)-isopropyl-N,N'-dibenzoylhydrazine. No biological activity is disclosed for those compounds.

In *J. Chem. Soc.*, 4191–4198 (1952), N,N'-di-n-propylhydrazine, N,N'-dibenzoylhydrazine and bis-3,5-dinitrobenzoyl are disclosed. No biological activity is disclosed for those compounds.

In 32 *Zhur. Obs. Khim.*, 2806–2809 (1962), N'-2,4-methyl-2,4-pentadiene-N,N'-dibenzoylhydrazine is disclosed. No biological activity is disclosed.

In 17 *Acta. Chim. Scand.*, 95–102 (1963), 2-benzoylthiobenzhydrazide $(C_6H_5-CS-NHNH-CO-C_6H_5)$ and certain hydrazone and hydrazine derivatives are disclosed including 1,2-dibenzoyl-benzylhydrazine. No biological activity is disclosd for those compounds.

In 25 *Zhur. Obs. Khim*, 1719–1723 (1955), N,N'-bis-cyclohexylhydrazine and N,N'-dibenzoylcyclohexylhydrazine are disclosed. No biological activity is disclosed for those compounds.

In *J. Chem. Soc.*, 4793–4800 (1964), certain dibenzoylhydrazine derivatives are disclosed including tribenzoylhydrazine and N,N'-dibenzoylcyclohexylhydrazine. No biological activity is disclosed for those compounds.

In 36 *J. Prakt. Chem.*, 197–201 (1967), certain dibenzoylhydrazine derivatives including N'-ethyl-; N'-n-propyl-; N'-isobutyl-; N'-neopentyl-; N'-n-heptyl-; and N'-cyclohexylmethyl-N,N'-dibenzoylhydrazines are disclosed. No biological activity is disclosed for those compounds.

In 26 *J.O.C.*, 4336–4340 (1961) N'-t-butyl-N,N'-di-(t-butoxycarbonyl)hydrazide is disclosed. No biological activity is disclosed In 41 *J.O.C.*, 3763–3765 (1976), N'-t-butyl-N-(phenylmethoxycarbonyl)-N'-(chlorocarbonyl)hydrazide is disclosed No biological activity is disclosed.

In 94 *J.A.C.S.*, 7406–7416 (1972) N'-T-butyl-N,N'-dimethoxycarbonylhydrazide is disclosed. No biological activity is disclosed.

In 43 *J.O.C.*, 808–815 (1978), N'-t-butyl-N-ethoxycarbonyl-N'-phenylaminocarbonylhydrazide and N'-t-butyl-N-ethoxycarbonyl-N'-methylaminocarbonylhydrazide are disclosed. No biological activity is disclosed for those compounds.

In 39 *J. Econ. Ent.*, 416–417 (1946), certain N-phenyl-N'-acylhydrazines are disclosed and evaluated for their toxicity against codling moth larvae.

The N'-substituted-N,N'-diacylhydrazines of the present invention differ from known compounds primarily by their N'-substituent and their N,N'-diacyl substituents.

Compounds of the present invention are also distinguished by their excellent insecticidal activity against insects of the order Lepidoptera without material adverse impact on beneficial insects.

SUMMARY OF THE INVENTION

In accordance with the present invention, there are provided insecticidal compositions and methods of using such compositions wherein the compositions comprise an agronomically acceptable carrier and an insecticidally effective amount of, or from about 0.0001% to about 99% by weight of the composition, compound having the formula:

$$\underset{H}{A-\overset{\overset{X}{\|}}{C}-N-\overset{\overset{R^1}{|}}{N}-\overset{\overset{X'}{\|}}{C}-B} \qquad I$$

wherein

X and X' are the same or different O, S or NR;

$R^1$ is unsubstituted ($C_3$–$C_{10}$) branched alkyl or a ($C_1$–$C_4$) straight chain alkyl substituted with one or two of the same or different ($C_3$–$C_6$)cycloalkyl; and A and B are unsubstituted phenyl or substituted phenyl where the substituents can be from one to five of the same or different halo; nitro; cyano; hydroxy; ($C_1$–$C_6$)alkyl; ($C_1$–$C_6$)haloalkyl; ($C_1$–$C_6$)cyanoalkyl; ($C_1$–$C_6$)alkoxy; ($C_1$–$C_6$)haloalkoxy; ($C_1$–$C_6$)alkoxyalkyl having independently the stated number of carbon atoms in each alkyl group; ($C_1$–$C_6$)alkoxyalkoxy having independently the stated number of carbon atoms in each alkyl group; carboxyoxy; ($C_1$–$C_6$)alkoxycarbonyloxy; ($C_2$–$C_6$)alkenyl optionally substituted with halo, cyano, ($C_1$–$C_4$)alkyl, ($C_1$–$C_4$)alkoxy, ($C_1$–$C_4$)haloalkoxy or ($C_1$–$C_4$)alkylthio; ($C_2$–$C_6$)alkenylcarbonyl; ($C_2$–$C_6$)alkadienyl; ($C_2$–$C_6$)alkynyl optionally substituted with halo, cyano, nitro, hydroxy, ($C_1$–$C_4$)alkyl, ($C_1$–$C_4$)alkoxy, ($C_1$–$C_4$)haloalkoxy or ($C_1$–$C_4$)alkylthio; carboxy; ($C_1$–$C_6$)carboxyalkyl; alkoxycarbonylalkyl having independently the stated number of carbon atoms in each alkyl group; —COR; ($C_1$–$C_6$)haloalkylcarbonyl; ($C_1$–$C_6$)cyanoalkylcarbonyl; ($C_1$–$C_6$)nitroalkylcarbonyl; ($C_1$–$C_6$)alkoxycarbonyl; ($C_1$–$C_6$)haloalkoxycarbonyl; ($C_1$–$C_6$)alkanoyloxy; amino, ($C_1$–$C_6$)alkylamino or ($C_1$–$C_6$)dialkylamino having independently the stated number of carbon atoms in each alkyl group; amino or ($C_1$–$C_6$)alkylamino where the N of the amino or ($C_1$–$C_6$)alkylamino is substituted with hydroxy, ($C_1$–$C_4$)alkoxy or ($C_1$–$C_4$)alkylthio groups; —CONRR'; —OCONRR'; —NRCOR'; —NRCO$_2$R'; —OCONRCOR'; sulfhydryl; ($C_1$–$C_6$)alkylthio; ($C_1$–$C_6$)haloalkylthio; —NRCSR'; ($C_1$–$C_6$)alkylcarbonylthio; unsubstituted phenyl; substituted phenyl having one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number carbon atoms in each alkyl group; phenoxy where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino, ($C_1$–$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; or when two adjacent positions on the phenyl ring are substituted with alkoxy groups, these groups may be joined to form a 5 or 6 membered dioxolano or dioxano heterocyclic ring; or unsubstituted six-membered heterocycle or substituted six-membered heterocycle having one, two, three or four nitrogen atoms and two to fire nuclear carbon atoms where the substituents can be from one to three of the same or different halo; nitro; hydroxy; ($C_1$–$C_6$)alkyl; ($C_1$–$C_6$)alkoxy; ($C_1$–$C_6$)thioalkoxy carboxy; ($C_1$–$C_6$)alkoxycarbonyl; ($C_1$–$C_6$)carboxyalkyl ($C_1$–$C_6$)alkoxycarbonylalkyl having independently the stated number of carbon atoms in each alkyl group; —CONRR'; amino, ($C_1$–$C_6$)alkylamino or ($C_1$–$C_6$)dialkylamino having independently the stated number of carbon atoms in each alkyl group; —NRCOR'; ($C_1$–$C_6$)alkylthio unsubstituted phenyl; or substituted phenyl having one to three of the same or different halo, nitro, ($C_1$–$C_6$)alkyl, ($C_1$–$C_6$)haloalkyl, ($C_1$–$C_6$)alkoxy, ($C_1$–$C_6$)haloalkoxy, carboxy, ($C_1$–$C_4$)alkoxycarbonyl; or amino, ($C_1$–$C_6$)alkylamino or ($C_1$–$C_6$)dialkylamino having independently the stated number of carbon atoms in each alkyl group;

where R and R' are hydrogen or ($C_1$–$C_6$)alkyl; and agronomically acceptable salts thereof; where one of A or B is an unsubstituted or substituted six-membered heterocycle as defined above.

Also in accordance with the present invention, there are provided novel insecticidal compounds having the formula

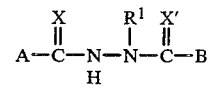

wherein

X and X' are the same or different O, S or NR;

$R^1$ is unsubstituted ($C_3$–$C_{10}$) branched alkyl or a ($C_1$–$C_4$) straight chain alkyl substituted with one or two of the same or different ($C_3$–$C_6$)cycloalkyl; and A and B are unsubstituted phenyl or substituted phenyl where the substituents can be from one to five of the same or different halo; nitroso; nitro; cyano; hydroxy; ($C_1$–$C_6$)alkyl; ($C_1$–$C_6$)haloalkyl; ($C_1$–$C_6$)cyanoalkyl; ($C_1$–$C_6$)alkoxy; ($C_1$–$C_6$)haloalkoxy; ($C_1$–$C_6$) alkoxyalkyl having independently the stated number of carbon atoms in each alkyl group; ($C_1$–$C_6$)alkoxyalkoxy having independently the stated number of carbon atoms in each alkyl group; carboxyoxy; ($C_1$–$C_6$)alkoxycarbonyloxy; ($C_2$–$C_6$)alkenyl optionally substituted with halo, cyano, ($C_1$–$C_4$)alkyl, ($C_1$–$C_4$)alkoxy, ($C_1$–$C_4$)haloalkoxy or ($C_1$–$C_4$)alkylthio; ($C_2$–$C_6$)alkenylcarbonyl; ($C_2$–$C_6$)alkadienyl; ($C_2$–$C_6$)alkynyl optionally substituted with halo, cyano, nitro, hydroxy, ($C_1$–$C_4$)alkyl, ($C_1$–$C_4$)alkoxy, ($C_1$–$C_4$)haloalkoxy or ($C_1$–$C_4$)alkylthio; carboxy; ($C_1$–$C_6$)carboxyalkyl; ($C_1$–$C_6$)alkoxycarbonylalkyl having independently the stated number of carbon atoms in each alkyl group; —COR; ($C_1$–$C_6$)haloalkylcarbonyl; ($C_1$–$C_6$)cyanoalkylcarbonyl; ($C_1$–$C_6$)nitroalkylcarbonyl; $(C_1-C_6)$alkoxycarbonyl; $(C_1-C_6)$haloalkoxycarbonyl; $(C_1-C_6)$alkanoyloxy; amino, $(C_1-C_6)$alkylamino or $(C_1-C_6)$dialkylamino having independently the stated number of carbon atoms in each alkyl group; amino or $(C_1-C_6)$alkylamino where the N of the amino or $(C_1-C_6)$alkylamino is substituted with hydroxy, $(C_1-C_4)$alkoxy or $(C_1-C_4)$alkylthio groups; —CONRR'; —OCONRR'; —NRCOR'; —NRCO$_2$R'; —OCONRCOR'; sulfhydryl; $(C_1-C_6)$alkylthio; $(C_{14}-C_6)$haloalkylthio; —NRCSR'; $(C_1-C_6)$alkylcarbonylthio; unsubstituted phenyl; substituted phenyl having one to three of the same or different halo, cyano, nitro, hydroxy, $(C_1-C_4)$alkyl $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; phenoxy where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; benzoyl where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; phenoxycarbonyl where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$ alkoxycarbonyl, $(C_1-C_4)$alkanoyloxy, amino, $(C_1-C_4)$alkylamino or $(C_1-C_4)$dialkylamino having independently the stated number of carbon atoms in each alkyl group; phenylthio where the phenyl ring is unsubstituted or substituted with one to three of the same or different halo, cyano, nitro, hydroxy, $(C_1-C_4)$alkyl, $(C_1-C_4)$alkoxy, carboxy, $(C_1-C_4)$alkoxycarbonyl $(C_1-C_4)$alkanoyloxy, amino, $(C_1-C_4)$alkylamino or $(C_1-C_4)$dialkylamino having independently the stated number of carbon atoms in each alkyl group; or when two adjacent positions on the phenyl ring are substituted with alkoxy groups, these groups may be joined to form a 5 or 6 membered dioxolano or dioxano heterocyclic ring; or unsubstituted six-membered heterocycle or substituted six-membered heterocycle having one, two, three or four nitrogen atoms and two to five nuclear carbon atoms where the substituents can be from one to three of the same or different halo; nitro; hydroxy; $(C_1-C_6)$alkyl; $(C_1-C_6)$alkoxy; $(C_1-C_6)$-thioalkoxy carboxy; $(C_1-C_6)$alkoxycarbonyl; $(C_1-C_6)$carboxyalkyl; $(C_1-C_6)$alkoxycarbonylalkyl having independently the stated number of carbon atoms in each alkyl group; —CONRR'; amino, $(C_1-C_4)$alkylamino or $(C_1-C_4)$dialkylamino having independently the stated number of carbon atoms in each alkyl group; —NRCOR'; $(C_1-C_6)$alkylthio; unsubstituted phenyl; or substituted phenyl having one to three of the same or different halo, nitro, $(C_1-C_6)$alkyl, $(C_1-C_6)$ haloalkyl, $(C_1-C_6)$alkoxy, $(C_1-C_6)$haloalkoxy carboxy, $(C_1-C_4)$alkoxycarbonyl, amino, $(C_1-C_4)$alkylamino or $(C_1-C_4$)dialkylamino having independently the stated number of carbon atoms in each alkyl group;

where R and R' are hydrogen or $(C_1-C_6)$alkyl; and agronomically acceptable salts thereof; where one of A or B is an unsubstituted or substituted six-membered heterocycle as defined above.

Further, in accordance with the present invention, there are provided methods of using these compounds and compositions.

DETAILED DESCRIPTION OF THE INVENTION

The term "halo" should be understood as including chloro, fluoro, bromo and iodo. The term "alkyl" by itself or as a part of another substituent, unless otherwise stated, includes straight or branched chain groups such as methyl, ethyl, n-propyl, isopropyl, n-butyl, t-butyl, isobutyl, neopentyl and the like and where indicated higher homologues and isomers such as n-octyl, isooctyl and the like. The term "haloalkyl" by itself or as part of another substituent is an alkyl group of the stated number of carbon atoms having one or more halo atoms bonded thereto such as chloromethyl, 1- or 2-bromoethyl, trifluoromethyl and the like. Analogously, "cyanoalkyl" by itself or as part of another group is an alkyl group of the stated number of carbon atoms having one or more cyano groups bonded thereto; "haloalkoxy" by itself or as part of another group is an alkoxy group of the stated number of carbon a toms having one or more halo a toms bonded thereto such as difluoromethoxy, trifluoromethoxy, 2-fluoroethoxy, 2,2,2-trifluoroethoxy and the like. "Alkenyl" and "alkynyl" by themselves or as part of another substituent comprise straight and branched chain groups of the stated number of carbon atoms. "Alkadienyl" is a straight or branched chain alkenyl group comprising two carbon-carbon double bonds that can be conjugated such as 1,3-butadienyl, cumulated such as 1,2-propadienyl or isolated such as 1,4-pentadienyl. Representative examples of six-membered heterocycles having one, two, three or four nitrogen atoms and two to five nuclear carbon atoms includes 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 3-pyrazinyl, 2-(1,3,5-triazinyl) 3-(1,2,4-triazinyl), 5-(1,2,4-triazinyl), 6-(1,2,4-triazinyl), 4-(1,2,3-triazinyl) and 5-(1,2,3-triazinyl).

Typical compounds within the scope of the present invention include, but are not limited to:

N'-t-butyl-N-(benzoyl)-N'-(isonicotinoyl) hydrazine

N'-t-butyl-N-(2-pyridylcarbonyl)-N'-(benzoyl)hydrazine

N'-t-butyl-N-(benzoyl)-N'-(nicotinoyl)hydrazine

N'-t-butyl-N-(nicotinoyl)-N'-(3,4-dichlorobenzoyl)hydrazine

N'-t-butyl-N-(benzoyl)-N'-(2-pyridylcarbonyl)hydrazine

N'-t-butyl-N-(nicotinoyl)-N'-(benzoyl)hydrazine

N'-t-butyl-N-(2-pyridylcarbonyl)-N'-(2-nitrobenzoyl)hydrazine

N'-t-butyl-N-(2-pyridylcarbonyl)-N'-(2-bromobenzoyl)hydrazine

N'-t-butyl-N-(4-ethylbenzoyl)-N'-(2-pyridylcarbonyl)hydrazine

N'-t-butyl-N-(4-trifluoromethoxybenzoyl)-N'-(2-pyridylcarbonyl)hydrazine

N'-t-butyl-N-(2-pyridylcarbonyl)-N'-(4-methylbenzoyl)hydrazine

N'-t-butyl-N-(2-pyridylcarbonyl)-N'-(3,4-dichlorobenzoyl)hydrazine
N'-t-butyl-N-(benzoyl)-N'-(pyrazinylcarbonyl)hydrazine
N'-t-butyl-N-(2-pyridylcarbonyl)-N'-(3,5-dimethylbenzoyl)hydrazine
N'-t-butyl-N-(5-bromonicotinoyl)-N'-(4-chlorobenzoyl)hydrazine
N'-t-butyl-N-(pyrazinylcarbonyl)-N'-(benzoyl)hydrazine
N'-t-butyl-(isonicotinoyl)-N'-(benzoyl)hydrazine
N'-t-butyl-2-pyridylcarbonyl-N'-(2-iodobenzoyl)hydrazine
N'-t-butyl-N-(2-pyridylcarbonyl)-N'-(2,4-dichlorobenzoyl)hydrazine
N'-t-butyl-N-(2-pyridylcarbonyl)-N'-(4-fluorobenzoyl)hydrazine
N'-t-butyl-N-(2-pyridylcarbonyl)-N'-(2-trifluoromethylbenzoyl)hydrazine
N'-t-butyl-(2-pyridylcarbonyl)-N'-(3-nitrobenzoyl)hydrazine
N'-t-butyl-N-(isonicotinoyl)-N'-(3-methylbenzoyl)hydrazine
N'-t-butyl-N-(2-bromonicotinoyl)-N'-(4-chlorobenzoyl)hydrazine
N'-t-butyl-N-(2-methylisonicotinoyl)-N'-(2-chlorobenzoyl)hydrazine
N'-t-butyl-N-(4-nitro-2-pyridylcarbonyl)-N'-(benzoyl)hydrazine
N'-t-butyl-N-(2,5-dichloronicotinoyl)-N'-(3-methylbenzoyl)hydrazine
N'-t-butyl-N-(5-methylnicotinoyl)-N'-(4-nitrobenzoyl)hydrazine
N'-t-butyl-N-(2-pyrimidinylcarbonyl)-N'-(3-methylbenzoyl)hydrazine
N'-t-butyl-N-(4-pyrimidinylcarbonyl)-N'-(2-bromobenzoyl)hydrazine
N'-t-butyl-N-(2-pyrimidinylcarbonyl)-N'-(4-chlorobenzoyl)hydrazine
N'-t-butyl-N-(2,3-dimethylbenzoyl)-N'-(nicotinoyl)hydrazine
N'-t-butyl-N-(2,3-dimethylbenzoyl)-N'-(isonicotinoyl)hydrazine
N'-t-butyl-N-(2-methyl, 3-chlorobenzoyl)-N'-(2-pyridylcarbonyl)hydrazine
N'-t-butyl-N-(3-pyridazinylcarbonyl)-N'-(benzoyl)hydrazine
N'-t-butyl-N-(4-pyridazinylcarbonyl)-N'-(4-chlorobenzoyl)hydrazine
N'-t-butyl-N-(4-pyridazinylcarbonyl)-N'-(3-methylbenzoyl)hydrazine
N'-t-butyl-N-(1,3,5-triazinyl-2-carbonyl)-N'-(4-chlorobenzoyl)hydrazine
N'-t-butyl-N-(4-ethylbenzoyl)-N'-(2-pyrimidinylcarbonyl)hydrazine
N'-t-butyl-N-(benzoyl)-N'-(2-pyrimidinylcarbonyl)hydrazine
N'-t-butyl-N-(2,3-dimethylbenzoyl)-N'-(4-pyrimidinylcarbonyl)hydrazine
N'-t-butyl-N-(4-methylbenzoyl)-N'-(4-pyridazinylcarbonyl)hydrazine
N'-t-butyl-N-(4-chlorobenzoyl)-N'-(1,3,5-triazinyl-2-carbonyl)hydrazine
N'-t-butyl-N-(3-chlorobenzoyl)-N'-(4-chloro-2pyrimidinylcarbonyl)hydrazine
N'-isopropyl-N-(benzoyl)-N'-(nicotinoyl)hydrazine
N'-isopropyl-N-(2-chlorobenzoyl)-N'-(2-pyrimidinylcarbonyl)hydrazine
N'-sec-butyl-N-(3-bromobenzoyl)-N'-(isonicotinoyl)hydrazine
N'-t-butyl-N-(2-chloro-3-pyridylcarbonyl)-N'-(3-methylbenzoyl)hydrazine
N'-t-butyl-N-(2,3-dimethylbenzoyl)-N'-(2-chloro-3pyridylcarbonyl)hydrazine
N'-t-butyl-N-(2-pyridylcarbonyl)-N'-(2-chloro, 5-methylbenzoyl)hydrazine
N'-t-butyl-N-(2-chloro-3-pyridylcarbonyl)-N'-(2-chloro, 5-methylbenzoyl)hydrazine
N'-t-butyl-N-(2-thiomethoxy-3-pyridylcarbonyl)-N'-(2-methylbenzoyl)hydrazine
N'-t-butyl-N-(2-thiomethoxy-3-pyridylcarbonyl)-N'-(3,4-dichlorobenzoyl)hydrazine
N'-t-butyl-N-(2-chloro-3-pyridylcarbonyl)-N'-(benzoyl)hydrazine
N'-t-butyl-N-(2-pyridylcarbonyl)-N'-(2-chloro, 4-fluorobenzoyl)hydrazine Insecticidal compounds of the present invention having very good activity for use in the insecticidal compositions and formulations of the present invention include those where, independently, X and X' are O or S;
$R^1$ is branched ($C_3$–$C_8$) alkyl; and
A and B are unsubstituted phenyl or substituted phenyl having one to three of the same or different halo; nitro; cyano; ($C_1$–$C_4$)alkyl; ($C_1$–$C_4$)haloalkyl; ($C_1$–$C_4$)cyanoalkyl; ($C_1$–$C_4$)alkoxy; ($C_1$–$C_4$)alkoxyalkyl having independently the stated number of carbon atoms in each alkyl group; —COZ; ($C_1$–$C_4$)alkoxycarbonyl; ($C_1$–$C_4$)alkanoyloxy; unsubstituted phenyl; substituted phenyl having one or two of the same or different halo, nitro, ($C_1$–$C_4$)alkyl, ($C_1$–$C_4$)alkoxy, carboxy, ($C_1$–$C_4$)alkoxycarbonyl, ($C_1$–$C_4$)alkanoyloxy or —NZZ'; or phenoxy where the phenyl ring is unsubstituted or substituted with one or two of the same or different halo, nitro, ($C_1$–$C_4$)alkyl, ($C_1$–$C_4$)alkoxy, carboxy, ($C_1$–$C_4$)alkoxycarbonyl, ($C_1$–$C_4$)alkanoyloxy; or —NZZ'; or
unsubstituted six-membered heterocycle or substituted six-membered heterocycle having one or two nitrogen atoms and 4 to 5 nuclear carbon atoms where the substituents can be one or two of the same or different halo; nitro; ($C_1$–$C_4$)alkyl; ($C_1$–$C_4$)alkoxy; —NZZ'; unsubstituted phenyl; or substituted phenyl having one or two of the same or different halo, nitro, ($C_1$–$C_4$)alkyl, ($C_1$–$C_4$)haloalkyl, ($C_1$–$C_4$)alkoxy, ($C_1$–$C_4$)haloalkoxy, carboxy or —NZZ';

where Z and Z' are hydrogen or ($C_1$–$C_4$)alkyl; and agronomically acceptable salts thereof, where one of A or B is an unsubstituted or substituted six-membered heterocycle as defined.

Because of their insecticidal activity, preferred compounds of the present invention for use in the insecticidal compositions and formulations of the present invention include those where, independently, X and X' are O;
$R^1$ is branched ($C_4$–$C_7$)alkyl; and
A and B are unsubstituted phenyl or substituted phenyl where the substituents can be from one to three of the same or different halo, nitro, ($C_1$–$C_4$)alkyl, ($C_1$–$C_4$)alkoxy or ($C_1$–$C_4$) haloalkyl; or
unsubstituted six-membered heterocycle or substituted six-membered heterocycle having one or two nitrogen atoms and four or five nuclear carbon atoms where the substituents can be one or two of the same or different halo, nitro, (C$_1$-C$_4$)alkyl or (C$_1$-C$_4$)alkoxy; and agronomically acceptable salts thereof, where one of A or B is an unsubstituted or substituted six-membered heterocycle as defined above.

Because of their outstanding insecticidal activity;, particularly preferred compounds of the present invention for use in the insecticidal compositions and formulations of the present invention include those where, independently, X and X' are O;

R$^1$ is t-butyl, neopentyl (2,2-dimethylpropyl) or 1,2,2-trimethylpropyl; and

A and B are unsubstituted phenyl or substituted phenyl where the substituents can be one or two of the same or different chloro, fluoro, bromo, iodo, nitro, methyl, ethyl, methoxy or trifluoromethyl; or unsubstituted pyridinyl or 1,4-pyrazinyl or substituted pyridinyl or 1,4-pyrazinyl where the substituent can be halo, nitro, (C$_1$-C$_4$)alkyl or (C$_1$-C$_4$)alkoxy; and agronomically acceptable salts thereof, where one of A or B is an unsubstituted or substituted six-membered heterocycle as defined above.

Those N'-substituted-N,N'-diacylhydrazines of Formula I which possess acidic or basic functional groups may be further reacted to form novel salts with appropriate bases or acids. These salts also exhibit pesticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. The ammonium salts include those in which the ammonium cation has the formula NR$^5$R$^6$R$^7$R$^8$ wherein each of R$^5$, R$^6$, R$^7$ and R$^8$ are independently hydrogen, hydroxy, (C$_1$-C$_4$)alkoxy, (C$_1$-C$_{20}$)alkyl, (C$_3$-C$_8$)alkenyl, (C$_3$-C$_8$)alkynyl, (C$_2$-C$_8$)hydroxyalkyl, (C$_2$-C$_8$)alkoxyalkyl, (C$_2$-C$_6$)aminoalkyl, (C$_2$-C$_6$)haloalkyl, amino, (C$_1$-C$_4$)alkyl- or (C$_1$-C$_4$)dialkylamino, substituted or unsubstituted phenyl, substituted or unsubstituted phenylalkyl, having up to four carbon atoms in the alkyl moiety, or any two of R$^5$, R$^6$, R$^7$ or R$^8$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of R$^5$, R$^6$, R$^7$ or R$^8$ can be taken together to form with the nitrogen atom a 5- or 6-membered aromatic heterocyclic ring, such as piperazole or pyridine. When R$^5$, R$^6$, R$^7$ or R$^8$ substituent in the ammonium group is a substituted phenyl or substituted phenylalkyl, the substituents on the phenyl and phenalkyl will generally be selected from halo, (C$_1$-C$_8$)alkyl, (C$_1$-C$_4$)alkoxy, hydroxy, nitro, trifluoromethyl, cyano, amino, (C$_1$-C$_4$)alkylthio and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxy-ethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as hydrochloride, hydrobromide, sulfate, nitrate, perchlorate, acetate, oxalate and the like.

The compounds of this invention or their precursors can be prepared according to the following processes.

PROCESS A $$\underset{II}{\text{Het}-\overset{O}{\overset{\|}{C}}-NH-NHR^1} + \underset{III}{Ar-\overset{O}{\overset{\|}{C}}-W} \xrightarrow[\text{Solvent}]{\text{Base}}$$

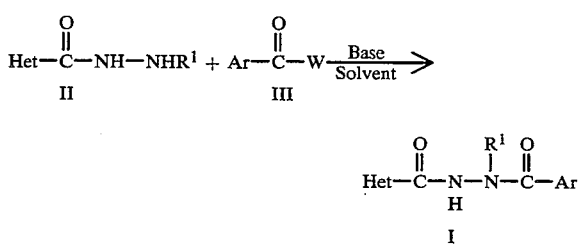

where Het is a six-membered heterocycle as defined above for Formula I, Ar is phenyl as defined above for Formula I, R$^1$ is as defined above for Formula I and W is a good leaving group such as halo, for example, chloro; an alkoxy, for example, ethoxy; a methyl sulfonate (—OSO$_2$CH$_3$); or an ester, for example, acetate (—OC(O)CH$_3$).

In Process A, a compound of Formula II is reacted with a compound of Formula III in the presence of a base in an inert or substantially inert solvent or mixture of solvents to afford the desired product of Formula I.

Examples of the compounds of Formula III which can be used in the above Process A include benzoyl chloride, 4-chlorobenzoyl chloride, 4-methylbenzoyl chloride, 3,5-dichlorobenzoyl chloride, 2-bromobenzoyl chloride, 3-cyanobenzoyl chloride, methyl benzoate, ethyl benzoate, benzoic acetic anhydride, benzoic methanesulfonic anhydride, and the like. The compounds of Formula III are generally commercially available or can be prepared by known procedures.

Suitable solvents for use in the above Process A include water; hydrocarbons such as toluene, xylene, hexane, heptane and the like; alcohols such as methanol, ethanol, isopropanol and the like; glyme, tetrahydrofuran; acetonitrile; pyridine; or haloalkanes such as methylene chloride; or mixtures of these solvents.

Preferred solvents are water, toluene, methylene chloride or a mixture of these solvents.

Examples of bases for use in the above Process A include tertiary amines such as triethylamine; pyridine; potassium carbonate; sodium carbonate; sodium bicarbonate; sodium hydroxide; or potassium hydroxide. Preferred bases are sodium hydroxide, or triethylamine.

The compounds of Formula II are prepared from commercially available compounds by procedures well known to those skilled in the art as described below.

The above Process A can be carried out at temperatures between about −50° C. and about 150° C. Preferably, when W is a halo radical, the reaction is carried out between about 0° C. and about 30° C. When W is alkoxy, the reaction is preferably carried out between about 100° C. and about 150° C. When W is methyl sulfonate, the reaction is preferably carried out between about −20° C. to about 20° C. When W is an ester, the reaction is preferably carried out between about 0° C. and about 50° C.

Preparation of the compounds of the present invention by Process A is preferably carried out at about atmospheric pressure, although higher or lower pressures can be used if desired.

Substantially equimolar amounts of reactants are preferably used in Process A, although higher or lower amounts can be used if desired.

Generally, about one equivalent of base is used per equivalent of the reactant of Formula III.

PROCESS B

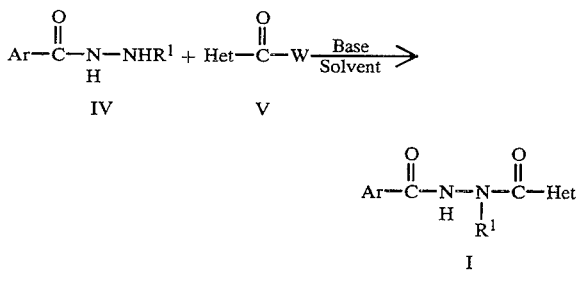

where Ar is phenyl as defined above for Formula I, $R^1$ is as defined above for Formula I, Het is a six-membered heterocycle as defined above for Formula I and W is a good leaving group such as halo, for example, chloro; an alkoxy, for example, ethoxy; methyl sulfonate (—O-SO$_2$CH$_3$); or an ester, for example, acetate (—OC(O)CH$_3$).

In Process B, an N'-substituted-N-benzoylhydrazine of Formula IV is reacted with a compound of Formula V in the presence of a base in an inert or substantially inert solvent or mixture of solvents to afford the desired product of Formula I.

Examples of the compounds of Formula IV which can be used in the above Process B include N'-isopropyl-N-benzoylhydrazine; N'-sec-butyl-N-benzoylhydrazine; N'-(1-methyl)neopentyl-N-benzoylhydrazine; N'-neopentyl-N-benzoylhydrazine; N'-isobutyl-N-benzoylhydrazine; N'-(1,2,2-trimethylpropyl)-N-benzoylhydrazine; N'-diisopropylmethyl-N-benzoylhydrazine; N'-t-butyl-N-benzoylhydrazine; N'-t-butyl-N-(4-methylbenzoyl)hydrazine; N'-t-butyl-N-(4-chlorobenzoyl)hydrazine; and the like.

The compounds of Formula V are generally commercially available or are prepared from commercially available compounds by procedures well known to those skilled in the art as described below.

Suitable solvents for use in the above Process B include water; hydrocarbons such as toluene, xylene, hexane, heptane and the like; alcohols such as methanol, ethanol, isopropanol and the like; glyme, tetrahydrofuran; acetonitrile; pyridine; or haloalkanes such as methylene chloride; or mixtures of these solvents. Preferred solvents are water, toluene, methylene chloride or a mixture of these solvents.

Examples of bases suitable for use in the above Process B include tertiary amines such as triethylamine; pyridine; potassium carbonate; sodium hydroxide; or potassium hydroxide. Preferred bases are sodium hydroxide, or triethylamine.

The above Process B can be carried out at temperatures between about −50 ° C. and about 150° C. Preferably, when W is a halo radical, the reaction is carried out between about 0° C. and about 30° C. When W is alkoxy, the reaction is preferably carried out between about 100° C. and about 150° C. When W is methyl sulfonate, the reaction is preferably carried out between about −20° C. to about 20° C. When W is an ester, the reaction is preferably carried out between about 0° C. and about 50° C.

Preparation of the compounds of the present invention by Process B is preferably carried out at about atmospheric pressure, although higher or lower pressures can be used if desired.

Substantially equimolar amounts of reactants are preferably used in Process B, although higher or lower amounts can be used, if desired.

Generally, about one equivalent of base is used per equivalent of the reactant of Formula V.

PROCESS C

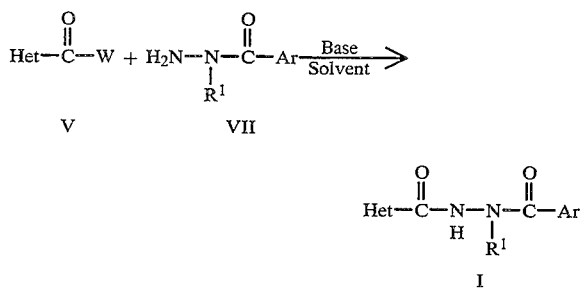

where Ar is phenyl as defined above for Formula I, Het is a six-membered heterocycle as defined above for Formula I, $R^1$ is as defined above for Formula I and W is a good leaving group such as halo, for example, chloro; an alkoxy, for example, ethoxy; methyl sulfonate (—OSO$_2$CH$_3$); or an ester, for example, acetate (—OC(O)CH$_3$).

In Process C, an N'-substituted-N'-benzoylhydrazine of Formula VII is reacted with a compound of Formula V in the presence of a base in an inert or substantially inert solvent or mixture of solvents to afford the desired product of Formula I.

The compounds of Formula V are generally commercially available or can be prepared from commercially available compounds by procedures well known to those skilled in the art as described below.

Examples of the compounds of Formula VII which can be used in the above Process C include N'-t-butyl-N'-benzoylhydrazine; N'-t-butyl-N'-(3-methylbenzoyl)hydrazine; N'-t-butyl-N'-(4-chlorobenzoyl)hydrazine; N'-t-butyl-N'-(2-fluorobenzoyl)hydrazine; N'-isopropyl-N'-benzoylhydrazine; N'-neopentyl-N'-(4-chlorobenzoyl)hydrazine, and the like.

Suitable solvents for use in the above Process C include water; hydrocarbons such as toluene, xylene, hexane, heptane and the like; alcohols such as methanol, ethanol, isopropanol and the like; glyme; tetrahydrofuran; acetonitrile; pyridine; or haloalkanes such as methylene chloride; or mixtures of these solvents. Preferred solvents are water, toluene, methylene chloride or a mixture of these solvents.

Examples of bases suitable for use in the above Process C includes tertiary amines such as triethylamine; pyridine; potassium carbonate; sodium carbonate; sodium bicarbonate; sodium hydroxide; or potassium hydroxide. Preferred bases are sodium hydroxide, or triethylamine.

The above Process C can be carried out at temperatures between about −50° C. and about 150° C. Preferably, when W is a halo radical, the reaction is carried out between about 0° C. and about 30° C. When W is alkoxy, the reaction is preferably carried out between about 100° C. and about 150° C. When W is methyl sulfonate, the reaction is preferably carried out between about −20° C. to about 20° C. When W is an ester, the reaction is preferably carried out between about 0° C. and about 50° C.

Preparation of the compounds of the present invention by Process C is preferably carried out at about atmospheric pressure, although higher or lower pressures can be used if desired.

Substantially equimolar amounts of reactants are preferably used in Process C, although higher or lower amounts can be used if desired.

Generally, about one equivalent of base is used per equivalent of the reactant of Formula V.

The compounds of Formula II are prepared by procedures well known to those skilled in the art. By way of examples, a suitably substituted hydrazine (such as t-butylhydrazine) is reacted with a heterocyclic ester (such as ethyl 2-pyridylcarboxylate) in an inert or substantially inert solvent or mixture of solvents (such as ethanol), with heat, to afford the compounds of Formula II (such as N'-t-butyl-N-(2-pyridylcarbonyl)hydrazine; a heterocycle carboxylic acid (such as 2-carboxypyrazine) is reacted with methanesulfonyl chloride in the presence of a base (such as triethylamine) in an inert or substantially inert solvent or mixture of solvents (such as methylene chloride) to afford the corresponding mixed anhydride (such as pyrazine carboxylicmethanesulfonic anhydride which is then reacted with a suitably substituted hydrazine (such as t-butylhydrazine) in the presence of a base (such as triethylamine) in an inert or substantially inert solvent or mixture of solvents (such as methylene chloride) to afford the compounds of Formula II (such as N'-t-butyl-N-(2-pyrazinecarbonyl)hydrazine); a suitably substituted hydrazine (such as t-butylhydrazine) is reacted with a heterocyclic carboxylic acid halide (such as 3-pyridinecarboxylic acid chloride) in the presence of a base (such as sodium hydroxide) in an inert or substantially inert solvent or mixture of solvents (such as toluene) to afford the compounds of Formula II (such as N'-t-butyl-N-(3-pyridinecarbonyl)hydrazine).

Suitably substituted hydrazines such as t-butylhydrazine, isopropylhydrazine and the like are commercially available or can be prepared by procedures well known to those skilled in the art.

The compounds of Formula IV are prepared from commercially available materials by procedures known to those skilled in the art. By way of example, a suitably substituted hydrazine (such as t-butylhydrazine) is reacted with a benzoyl chloride (such as benzoyl chloride, 3-methylbenzoyl chloride or 4-chlorobenzoyl chloride) in the presence of a base (such as aqueous sodium hydroxide) in an inert or substantially inert solvent or mixture of solvents (such as toluene) to afford the compounds of Formula IV (such as N'-t-butyl-N-benzoylhydrazine, N'-t-butyl-N-(3-methylbenzoyl)hydrazine or N'-t-butyl-(4-chlorobenzoyl)hydrazine).

The compounds of Formula V are commercially available, such as nicotinoyl chloride hydrochloride, isonicotinyol chloride hydrochloride and ethyl picolinate or can be prepared from commercially available materials by procedures known to those skilled in the art as described above.

The compounds of Formula VII can be prepared by procedures known to those skilled in the art from commercially available reactants. By way of example, a suitably substituted hydrazine (such as t-butylhydrazine) is reacted with an aldehyde or ketone (such as acetone) in the presence of a base (such as triethylamine) to afford a hydrazone which is then reacted with a benzoyl chloride in an inert or substantially inert solvent or mixture of solvents in the presence of a base (such as sodium hydroxide) to afford an N'-substituted-N'-benzoylhydrazone which is then reacted with an acid (such as hydrochloric acid) to afford the compound of Formula VII. Alternatively, a suitably substituted hydrazine (such as t-butylhydrazine) is reacted with di-tert-butyldicarbonate in an inert or substantially inert solvent or mixture of solvents (such as toluene/water) to afford an N'-t-butyl-N-t-butoxycarbonylhydrazine which is then reacted with a benzoylchloride in an inert or substantially inert solvent or mixture of solvents to afford an N'-t-butyl-N'-benzoyl-N-t-butoxycarbonylhydrazine which is then reacted with an acid to afford the desired compound of Formula VII.

Modifications to the above processes may be necessary to accommodate reactive functionalities of particular A and/or B substituents. Such modifications would be apparent and known to those skilled in the art.

It will be appreciated by those skilled in the art that electronic attractive forces may give rise to more than one isomer of the compounds of Formula I. There may be a difference in properties such as biological activity and physical characteristics between such isomers. It is believed the procedures for making the compounds of Formula I described herein will not preferentially afford one isomer over another. Separation of a specific isomer can be accomplished by standard techniques well known to those skilled in the art such as silica gel chromatography.

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more hydroxy or carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme and the like; dioxane; tetrahydrofuran; alcohols such as methanol, ethanol, isopropanol and the like. When metal hydrides are used as reagents, useful solvents include nonhydroxylic solvents, for example, ethers such as dioxane, glyme, diethylether and the like; tetrahydrofuran; hydrocarbons such as toluene, xylene, hexane, pentane, heptane, octane and the like; dimethylformamide, and the like. When amines are used as reagents, useful solvents include alcohols, such as methanol or ethanol; hydrocarbons, such as toluene, xylene, hexane and the like; tetrahydrofuran; glyme; dioxane; or water. When ammonium salts are used as reagents, useful solvents include water; alcohols, such as methanol or ethanol; glyme; tetrahydrofuran; or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acid with a compound Formula I having a basic functional group in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out at from about −10° C. to about 100° C., preferably at about room temperature.

The following examples will further illustrate this invention but are not intended to limit it in any way. In Table I, six-membered heterocyclic derivatives of some N'-substituted-N,N'-diacyl hydrazines of the present invention that have been made are listed. The structure of these compounds was confirmed by NMR and in some cases by IR and/or elemental analysis. Specific illustrative preparation of the compounds Examples 1, 2, 3, 6, 8, 12, 16, 17, 18 and, 33A and 33B are described after Table I.

TABLE I $$\begin{array}{c} \quad\quad X \quad\quad R^1 \quad X' \\ \quad\quad \| \quad\quad\, | \quad\quad \| \\ A-C-N-N-C-B \\ \quad\quad\quad\, H \end{array}$$

| Ex. No. | X | X' | $R^1$ | A | B | m.p. °C. |
|---|---|---|---|---|---|---|
| 1 | O | O | —C(CH$_3$)$_3$ | —C$_6$H$_5$ | 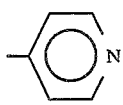 3-pyridyl | >210 |
| 2 | O | O | —C(CH$_3$)$_3$ | 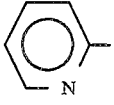 3-pyridyl | —C$_6$H$_5$ | >210 |
| 3 | O | O | —C(CH$_3$)$_3$ | —C$_6$H$_5$ | 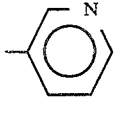 4-pyridyl | 60–63 |
| 4 | O | O | —C(CH$_3$)$_3$ | 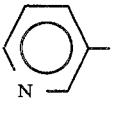 2-pyridyl | —C$_6$H$_3$Cl$_2$-3,4 | 231–233 |
| 5 | O | O | —C(CH$_3$)$_3$ | 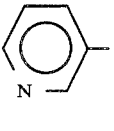 2-pyridyl | —C$_6$H$_5$ | 171–172 |
| 6 | O | O | —C(CH$_3$)$_3$ | 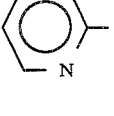 3-pyridyl | —C$_6$H$_4$NO$_2$-2 | 137–140 |
| 7 | O | O | —C(CH$_3$)$_3$ | 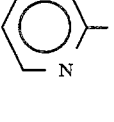 3-pyridyl | —C$_6$H$_4$CH$_2$CH$_3$-4 | 207–208 |
| 8 | O | O | —C(CH$_3$)$_3$ | 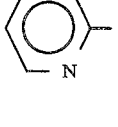 3-pyridyl | —C$_6$H$_4$Br-2 | 179–180 |

TABLE I-continued $$\underset{H}{\overset{X}{\underset{\|}{A-C}}-N}-\overset{R^1}{\underset{|}{N}}-\overset{X'}{\underset{\|}{C}}-B$$

| Ex. No. | X | X' | R¹ | A | B | m.p. °C. |
|---|---|---|---|---|---|---|
| 9 | O | O | —C(CH₃)₃ | —C₆H₄CH₂CH₃-4 | 3-pyridyl | 129–133 |
| 10 | O | O | —C(CH₃)₃ | —C₆H₄OCF₃-4 | 3-pyridyl | 140–145 |
| 11 | O | O | —C(CH₃)₃ | 2-pyridyl | —C₆H₄CH₃-3 | 174–175 |
| 12 | O | O | —C(CH₃)₃ | 2-pyridyl | —C₆H₃Cl₂-3,4 | 175–178 |
| 13 | O | O | —C(CH₃)₃ | CH₃(CH₂)₃-pyridyl | —C₆H₅ | 135–140 |
| 14 | O | O | —C(CH₃)₃ | —C₆H₅ | pyrazinyl | 135–140 |
| 15 | O | O | —C(CH₃)₃ | 2-pyridyl | —C₆H₃(CH₃)₂-3,5 | 162–164 |
| 16 | O | O | —C(CH₃)₃ | Br-pyridyl | —C₆H₄Cl-4 | 193–197 |
| 17 | O | O | —C(CH₃)₃ | pyridyl | —C₆H₅ | 181–183 |
| 18 | O | O | —C(CH₃)₃ | pyridyl | —C₆H₅ | 196–198 |
| 19 | O | O | —C(CH₃)₃ | pyridyl | —C₆H₄OCH₃-4 | 208–210 |
| 20 | O | O | —C(CH₃)₃ | 2-pyridyl | —C₆H₄I-2 | 175 |

TABLE I-continued $$\underset{H}{A-\overset{\overset{X}{\|}}{C}-N}-\overset{R^1}{\underset{}{N}}-\overset{\overset{X'}{\|}}{C}-B$$

| Ex. No. | X | X' | R¹ | A | B | m.p. °C. |
|---|---|---|---|---|---|---|
| 21 | O | O | —C(CH₃)₃ | 2-pyridyl | —C₆H₃Cl₂-2,4 | 97–98 |
| 22 | O | O | —C(CH₃)₃ | 2-pyridyl | —C₆H₄CF₃-2 | 215–218 |
| 23 | O | O | —C(CH₃)₃ | 2-pyridyl | —C₆H₄CF₃-2 | 126–128 |
| 24 | O | O | —C(CH₃)₃ | 2-pyridyl | —C₆H₄NO₂-3 | 176–179 |
| 25 | O | O | —C(CH₃)₃ | 3-pyridyl | —C₆H₄CH₃-3 | 203–206 |
| 26 | O | O | —C(CH₃)₃ | 2-pyridyl | —C₆H₄Cl-2 | 160–162 |
| 27 | O | O | —C(CH₃)₃ | 2-pyridyl | —C₆H₄OCH₃-3 | 225–228 |
| 28 | O | O | —C(CH₃)₃ | 2-pyridyl | —C₆H₄F-4 | 201–205 |
| 29 | O | O | —C(CH₃)₃ | —C₆H₅ | 6-(OSO₂CH₃)-2-pyridyl | 176–178 |
| 30 | O | O | —C(CH₃)₃ | pyrazinyl | —C₆H₄F-4 | >250 |
| 31 | O | O | —C(CH₃)₃ | —C₆H₅ | pyrazinyl | 188–190 |
| 32 | O | O | —C(CH₃)₃ | 2-pyridyl | —C₆H₃(CH₃)₂-2,3 | 157–158 |

TABLE I-continued
$$\underset{H}{\overset{X}{\underset{\|}{A-C-N}}-\overset{R^1}{\underset{|}{N}}-\overset{X'}{\underset{\|}{C-B}}}$$
| Ex. No. | X | X' | R¹ | A | B | m.p. °C. |
|---|---|---|---|---|---|---|
| 33A | O | O | —C(CH₃)₃ | —C₆H₅ | 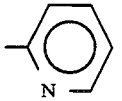 | 220 |
| 33B | O | O | —C(CH₃)₃ | —C₆H₅ | 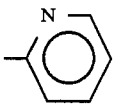 | 173 |
| 34 | O | O | —C(CH₃)₃ | 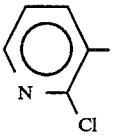 | —C₆H₄CH₃-3 | 200–202 |
| 35 | O | O | —C(CH₃)₃ | —C₆H₃(CH₃)₂-2,3 | 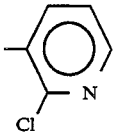 | 190 |
| 36 | O | O | —C(CH₃)₃ | 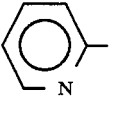 | —C₆H₃ClCH₃-2,5 | 115 |
| 37 | O | O | —C(CH₃)₃ | 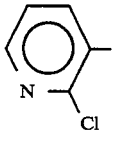 | —C₆H₃ClCH₃-2,5 | 115–120 |
| 38 | O | O | —C(CH₃)₃ | 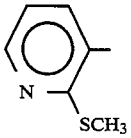 | —C₆H₄CH₃-3 | 214–219 |
| 39 | O | O | —C(CH₃)₃ | 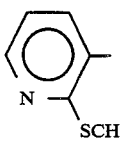 | —C₆H₃Cl₂-3,4 | >225 |
| 40 | O | O | —C(CH₃)₃ | 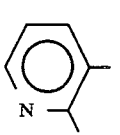 | —C₆H₅ | 241–243 |
| 41 | O | O | —C(CH₃)₃ | 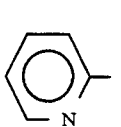 | —C₆H₃ClF-2,4 | 152–155 |

EXAMPLE 1

Preparation of N'-t-butyl-N-benzoyl-N'-isonicotinoylhydrazine

N'-t-butyl-N-benzoylhydrazine (1.0 g, 0.0052 mol) was suspended in 20 ml of toluene. Isonicotinoyl chloride hydrochloride (0.93 g, 0.0052 mol) was added and then a solution of sodium hydroxide (1.25 g of 50% aqueous NaOH) in 5 ml of water was added dropwise. After stirring at 23° C. for 2 hours, the solids were removed by filtration, washed with water and dried in air. The crude product was chromatographed on silica gel using 5% methanol/methylene chloride as eluant to afford pure N'-t-butyl-N-benzoyl-N'-isonicotinoylhydrazine. m.p. >210° C.

EXAMPLE 2

Preparation of N'-t-butyl-N-(2-pyridinecarbonyl)-N'-benzoylhydrazine

A solution of N'-t-butyl-N-(2-pyridinecarbonyl)hydrazine (1.0 g, 0.00518 mol) in 20 ml of toluene at 23° C. was treated sequentially with 50% sodium hydroxide (1.3 g) and benzoyl chloride (0.728 g). The mixture was stirred overnight. The solids were removed by filtration and washed with water to afford N'-t-butyl-N-(2-pyridinecarbonyl)-N'-benzoylhydrazine.

EXAMPLE 3

Preparation of N'-t-butyl-N-benzoyl-N'-nicotinoylhydrazine

A solution of N'-t-butyl-N-benzoylhydrazine (2.0 g) and nicotinoyl chloride hydrochloride in 20 ml of methylene chloride at 23° C. was treated dropwise with triethylamine (4 ml). The reaction mixture was stirred at 23° C. for 0.5 hours. Solids were removed by filtration. The filtrate was diluted with N/10 HCl and ether. The layers were separated and the organic layer was washed with N/10 HCl. The aqueous layer was neutralized with solid sodium bicarbonate and extracted with ether. The ether extracts were treated with charcoal and then dried with magnesium sulfate. Evaporation of solvents afforded a yellow oil which was chromatographed on silica gel using 10% $CH_3OH$, 40% $CH_2Cl_2$, 50% $Et_2O$ as eluant to afford N'-t-butyl-N-benzoyl-N'-nicotinoylhydrazine as a yellow foam. m.p. 60°–63° C.

EXAMPLE 6

Preparation of N'-t-butyl-N-(2-pyridinecarbonyl)-N'-(2-nitrobenzoyl)-hydrazine A solution of N'-t-butyl-N-(2-pyridinecarbonyl)hydrazine (1.0 g, 0.00518 mol) in 20 ml of toluene was treated dropwise simultaneously with a solution of sodium hydroxide (1.24 g of 50% aqueous solution) in 5 ml of water and 2-nitrobenzoyl chloride (0.96 g). The resulting mixture was stirred at 23° C. overnight. Water was added and the mixture was extracted with ether. A second extraction was performed with methylene chloride and the combined organic extracts were dried over magnesium sulfate. Evaporation afforded 0.4 g of N'-t-butyl-N-(2-pyridinecarbonyl)-N'(2-nitrobenzoyl)hydrazine as a yellow solid. m.p. 137°–140° C.

EXAMPLE 8

Preparation of N'-t-butyl-N-(2-pyridinecarbonyl)-N'-(2-bromobenzoyl)hydrazine An aqueous solution of sodium hydroxide (1.24 g of 50% NaOH diluted with 5 ml of water) was added to a solution of N'-t-butyl-N-(2-pyridinecarbonyl)hydrazine (1.0 g, 0.00518 mol) in 20 ml of toluene at 23° C. The mixture was cooled and treated with 2-bromobenzoyl chloride (1.137 g, 0.00518 mol). The mixture was then stirred at 23° C. overnight. The solids were removed by filtration, washed with water and dried to afford 0.96 g of N'-t-butyl-N-(2-pyridinecarbonyl)-N'-(2-bromobenzoyl)hydrazine as a white solid. m.p. 179°–180° C.

EXAMPLE 12

Preparation of N'-t-butyl-N-(2-pyridinecarbonyl)-N'-(3,4-dichlorobenzoyl)hydrazine A solution of N'-t-butyl-N-(2-pyridinecarbonyl)hydrazine (0.5 g) in 10 ml of toluene was treated with 50% sodium hydroxide (0.61 g). 3,4-dichlorobenzoyl chloride (0.6 g) was added and the mixture was stirred rapidly for 4 hours at 23° C. and then was allowed to stand for 48 hours. The solids were removed by filtration and washed with water to afford 0.75 g of N'-t-butyl-N-(2-pyridinecarbonyl)-N'-(3,4-dichlorobenzoyl)hydrazine as a white solid. m.p. 175°–178° C.

EXAMPLE 16

Preparation of N'-t-butyl-N-(5-bromonicotinoyl-N'-(4-chlorobenzoyl)-hydrazine N'-t-butyl-N'-(4-chlorobenzoyl)hydrazine was prepared substantially according to the procedure for preparing N'-t-butyl-N'-benzoylhydrazine described for Example 17 except 4-chlorobenzoyl chloride was used in place of benzoyl chloride.

A solution of N'-t-butyl-N'-(4-chlorobenzoyl)hydrazine (0.5 g, 0.0022 mol) and 5-bromonicotinic acid (0.44 g, 0.0022 mol) in 10 ml of methylene chloride containing triethylamine (0.33 g) was added to a solution of methanesulfonyl chloride (0.25 g, 0.0022 mol) in 10 ml of methylene chloride at 0° C. The resulting mixture was stirred at 23° C. for 2 hours and then was allowed to stand overnight at 23° C. Aqueous sodium bicarbonate was added and the layers were separated. The aqueous layer was re-extracted with methylene chloride. The organic extracts were evaporated to give a yellow solid which was triturated with hexane/methylene chloride to afford N'-t-butyl-N-(5-bromonicotinoyl)-N'-(4-chlorobenzoyl)hydrazine as an off-white solid. m.p. 193°–197° C.

EXAMPLE 17

Preparation of N'-t-butyl-N-(pyrazinecarbonyl)-N'-benzoylhydrazine

To a mechanically stirred solution of t-butylhydrazine hydrochloride (51 g, 0.41 mol) in dioxane (100 ml) and water (50 ml), cooled in an ice bath was treated with 50% sodium hydroxide (32 g). The resulting mixture was treated dropwise with di-t-butyldicarbonate (92 g, 0.42 mol) over about one-half of an hour. After complete addition, the reaction mixture was warmed to room temperature and stirred for 2 hours. The resulting white solid was filtered off, washed with water and air-dried to afford 74 g of N'-t-butyl-N-t-butoxycarbonylhydrazine, m.p. 69°–71° C.

A mechanically stirred solution of N'-t-butyl-N-t-butoxycarbonylhydrazine (61 g, 0.32 mol) in toluene (120 ml) cooled in an ice bath, was treated dropwise and simultaneously with 50% sodium hydroxide (31 g) in water (50 ml) and benzoyl chloride (45 g). The addition was complete in 20 minutes and the resulting mixture was warmed to room temperature and allowed to stir for one hour. The resulting white solid was filtered, washed with water and air dried to afford 94 g of N-t-butoxycarbonyl-N'-benzoyl-N'-t-butylhydrazine, m.p. 167°–170° C.

To a mechanically stirred solution of N-t-butoxycarbonyl-N'-benzoyl-N'-t-butylhydrazine (52 g, 0.18 mol) in methanol (100 ml) was added concentrated hydrochloric acid (35 ml). The resulting mixture was stirred at room temperature for 4 days and then neutralized with saturated aqueous sodium bicarbonate. The resulting white solid was filtered, washed with water and dried under vacuum to afford N'-t-butyl-N'-benzoylhydrazine (39 g) m.p. 124°–125° C.

Triethylamine (1.0 g, 0.01 mol) was added to a solution of N'-t-butyl-N'-benzoylhydrazine (0.86 g, 0.0031 mol) and pyrazine carboxylic acid (0.56 g, 0.0045 mol) in 10 ml of methylene chloride at 23° C. This mixture was added to a solution of methanesulfonyl chloride (0.6 g, 0.0052 mol) in 10 ml of methylene chloride at 0° C. The mixture was stirred at 23° C. for 3 hours and then allowed to stand at 23° C. overnight. Aqueous sodium bicarbonate was added and the layers were separated. The organic extracts were evaporated to give crude product which was triturated with ether to afford N'-t-butyl-N-(pyrazinecarbonyl)-N'benzoylhydrazine as a white solid. m.p. 181°–183° C.

EXAMPLE 18

Preparation of
N'-t-butyl-N-isonicotinoyl-N'-benzoylhydrazine

A solution of N'-t-butyl-N'-benzoylhydrazine (0.5 g, 0.00026 mol) in 10 ml of toluene was treated with 50% sodium hydroxide (0.6 g) followed by isonicotinyl chloride hydrochloride (0.47 g, 0.0026 mol). The mixture was stirred at 23° C. overnight. The solids were removed by filtration and washed with water followed by ether to afford N'-t-butyl-N-isonicotinyl-N'-benzoylhydrazine.

EXAMPLE 22

Preparation of
N'-t-butyl-N-(2-pyridinecarbonyl)-N'-(4-fluorobenzoyl)hydrazine)

By substantially following the procedures described above for Example 2, except using 4-fluorobenzoyl chloride rather than benzoyl chloride, N'-t-butyl-N-(2-pyridinecarbonyl)-N'-(4-fluorobenzoyl)hydrazine was afforded.

EXAMPLES 33A AND 33B

Preparation of
N'-t-butyl-N'-(2-pyridinecarbonyl)-N-benzoylhydrazine

To a suspension of 2-picolinic acid (12.8 g, 0.104 mol.) in methylene chloride (80 ml) were added dropwise triethylamine (14 g, 0.139 mol.) in 10 ml methylene chloride followed by methanesulfonyl chloride (13 g, 0.113 mol.) in 10 ml methylene chloride at 0° C. The resulting mixture was stirred for half an hour before the dropwise addition of N'-t-butyl-N-benzoylhydrazine (20.0 g, 0.10 mole) in 80 ml methylene chloride at 0° C. to 23° C. The final dark brown mixture was allowed to stir at 23° C. for one hour, and to stand at 23° C. overnight.

Aqueous sodium bicarbonate was added and the layers were separated. The aqueous layer was reextracted with methylene chloride. The organic extracts were combined, and dried over magnesium sulfate. Evaporation under reduced pressure gave 25 g of a light green, brown solid. Recrystalization on a steam bath with ethyl acetate:hexane (80:20v/v) afforded a light yellow solid.

Column chromatography on silica gel, eluted first with methylene chloride and ether and then with ethyl acetate afforded two separate isomers of N'-t-butyl-N'-(2-pyridinecarbonyl)-N-benzoylhydrazine.

By following substantially the procedures in the processes described above and as exemplified by the preparation of the compounds of Examples 1, 2, 3, 6, 8, 12, 16, 18 and 33A and 33B, the compounds of Formula I are prepared.

As previously noted, the compounds of the present invention exhibit excellent insecticidal activity and are selective against insects of the order Lepidoptera.

In general, for the control of insects in agriculture, horticulture and forestry, the compounds of the present invention may be used at a dosage corresponding to from about 10 grams to about 10 kilograms of the active substance per hectare and from about 100 grams to about 5 kilograms per hectare of the active substance is preferred. The exact amount of dosage for a given situation can be routinely determined and depends on a variety of factors, for example, the substance used, the kind of insect, the formulation used, the state of the crop infested with the insect and the prevailing weather conditions. The term "insecticidal" as employed in the specification and claims of this application is to be construed as any means which adversely affects the existence or growth of the target insects. Such means can comprise a complete killing action, eradication, arresting in growth, inhibition, reducing in number or any combination thereof. The term "control" as employed in the specification and claims of this application is to be construed as meaning "insecticidal" or protecting plants from insect damage. By "insecticidally effective amount" is meant that dosage of active substance sufficient to exert insect "control."

The compounds of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations," (1973), edited by Wade Van Valkenburg. In these compositions and formulations, the active substance or substances are mixed with conventional inert agronomically acceptable (i.e., plant compatible and/or pesticidally inert) diluents or extenders such as solid carrier material or liquid carrier material, of the type usable in conventional compositions or formulations. By agronomically acceptable carrier is meant any substance which can be used to dissolve, disperse or diffuse the active ingredient in the composition without impairing the active ingredient's effectiveness and which by itself has no significant detrimental effect on the soil, equipment, desirable plants or agronomic environment. If desired, conventional adjuvants such as surfactants, stabilizers, antifoam agents and antidrift agents may also be added.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to the target pest, that includes at least one lethal or non-lethal toxicant. Lethal toxicants kill the pest upon ingesting the bait while non-lethal toxicants change the behavior, feeding habits and physiology of the pest for the purpose of control.

The invert emulsions are mainly used for air application, where large areas are treated with a comparatively small amount of preparation. The invert emulsion may be prepared in the spraying apparatus shortly; before, or even during, the spraying operation by emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cottonseed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or nonionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolysates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1% and 99% by weight, preferably between about 0.1% and 90% by weight, and more preferably between about 1% and 75% by weight, of the mixture. Carrier composition mixtures suitable for direct application or field application generally contemplate those in which the active compound is used in an amount substantially between about 0.0001% and 5%, preferably between about 0.001% and 3%, by weight of the mixture. Thus the present invention contemplates overall formulations and compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant (e.g., a surface-active agent, such as an emulsifying agent and/or a dispersing agent), and an amount of the active compound generally, between about 0.0001% and about 99% by weight of the composition, preferably between about 0.001% and about 90% by weight of the composition, and more preferably between about 0.01% and about 75% by weight of the composition, which is effective for the purpose in question.

The active compounds can be applied as sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and of ten amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of killing, combatting or controlling insects, which comprises contacting insects with a correspondingly combative or toxic amount (i.e., an insecticidally effective amount) of at least one active compound of the invention alone or together with a carrier vehicle (composition or formulation) as noted above. The term "contacting" as employed in the specification and claims of this application is to be construed as applying to at least one of (a) such insects and (b) the corresponding habitat thereof (i.e., the locus to be protected, for example, to a growing crop or to an area where a crop is to be grown) the active compound of this invention alone or as a constituent of a composition or formulation. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example, pumice and attaclay), or chopped tobacco stems or the like.

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and similar substances. Alternatively organic carrier materials such as, for example, ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance optionally dissolved in a volatile solvent such as acetone, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products. In the case of flowables, a liquid inert carrier such as water is also included.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight depending upon toxicant solubility. A suitable liquid highly concentrated primary composition other than an emulsifiable concentrate is a solution of the active substance in a liquid which is readily miscible with water, for example, acetone, to which solution a dispersant and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e., preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients, the preparations according to the invention may also contain other substances commonly used in preparations of this kind.

For example, a lubricant, such as calcium stearate or magnesium stearate, may be added to a wettable powder or to a mixture to be granulated. Furthermore, there may, for example, be added "adhesives" such as polyvinylalcohol cellulose derivatives or other colloidal materials, such as casein, to improve the adherence of this pesticide to the surface to be protected.

Representative preparation of compositions and formulations including the compounds of the present invention are set forth below as Examples A through I by way of illustration but not limitation.

EXAMPLE A

Granular

| Ingredient | %/wt. |
| --- | --- |
| Toxicant and toxicant impurities | 0.25 |
| Triton ® X-305 (binder) (Octylphenyl-30-ethylene oxide ethanol) | 0.25 |
| Agsorb ® 24/48 (diluent) (Montmorillonite clay) | 99.50 |

Preparation: The toxicant and Triton ® X-305 are dissolved into methylene chloride and the mixture is added to the Agsorb ® with continuous mixing. The methylene chloride is then allowed to evaporate.

EXAMPLE B

Dust

| Ingredient | %/wt. |
| --- | --- |
| Toxicant and toxicant impurities | 1.0 |
| Talc | 99.0 |

Preparation: Toxicant is dissolved in excess acetone and the mixture is impregnated onto the talc. The acetone is then permitted to evaporate.

EXAMPLE C

Wettable Powder

| Ingredient | %/wt. |
| --- | --- |
| Toxicant and toxicant impurities | 31.3 |
| Duponal ® WA Dry (wetter) (Sodium lauryl sulfate) | 2.0 |
| Reax ® 45A (dispersant) (Sodium liqnin sulfonate) | 5.0 |
| Barden clay (diluent) | 31.7 |
| HiSil ® 233 (diluent) (Sodium silica) | 30.0 |

Preparation: The toxicant, optionally dissolved in a volatile solvent, is absorbed onto the Barden clay and HiSil ® carriers. The Duponal ® and Reax ® are then added and the entire dry mixture blended until homogeneous. The composition is then micronized to a fine particle size.

EXAMPLE D

Emulsifiable Concentrate

| Ingredient | %/wt. |
| --- | --- |
| Toxicant and toxicant impurities | 15.0 |
| Sponto ® 232T (emulsifier) (Anionic and nonionic blend of the following surfactants: calcium dodecyl benzene sulfonate; and ethoxylated alkylphenol) | 6.0 |
| Sponto ® 234T (emulsifier) (Anionic and nonionic blend of the following surfactants: calcium dodecyl benzene sulfonate; and ethoxylated alkylphenol) | 4.0 |
| Cyclohexanone (solvent) | 22.5 |
| Tenneco ® 500-100 (solvent) (Aromatic solvent mixture principally comprising xylene, cumene and ethyl benzene having a boiling point range of 290–345° F.) | 52.5 |

Preparation: All ingredients are mixed together with continuous agitation until a homogeneous clear solution is obtained.

EXAMPLE E

Aerosol

| Ingredient | %/wt. |
| --- | --- |
| Toxicant and toxicant impurities | 0.5 |
| Freon 12 | 99.5 |

Preparation: The components are mixed and packaged under pressure in a suitable container equipped with a release spray valve.

EXAMPLE F

Fumigating Candle or Fumigating Powder

| Ingredient | %/wt. |
| --- | --- |
| Toxicant and toxicant impurities | 1.0 |
| Wood dust | 96.0 |
| Starch | 3.0 |

Preparation: Toxicant, wood dust, and starch are blended together and then molded into a candle using a small amount of water to activate the starch.

EXAMPLE G

Bait

| Ingredient | %/wt. |
| --- | --- |
| Toxicant and toxicant impurities | 1.00 |
| Wheat Bran (carrier and attractant) | 89.95 |
| Corn Syrup (attractant) | 7.00 |
| Corn Oil (attractant) | 2.00 |
| Kathon ® 4200 (preservative) (2-n-octyl-4-isothiazolin-3-one) | 0.05 |

Preparation: The corn oil and corn syrup are added to the wheat bran with adequate mixing. The toxicant and Kathon ® are premixed with excess acetone and this solution is added to the wheat bran base with continued mixing. The acetone is then permitted to evaporate.

| Ingredient | %/wt. |
| --- | --- |
| Toxicant and toxicant impurities | 0.06 |
| Granulated Sugar (carrier and attractant) | 99.94 |

EXAMPLE H

Pellet

Same as Example G, Method A, with this addition: the bait composition is formed into $\frac{1}{4}''$ diameter by $\frac{3}{8}''$ long pellets using a silicate die and press apparatus.

EXAMPLE I

Flowable

| Ingredient | %/Wt. |
| --- | --- |
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| HiSil ® 233 (diluent) (Sodium silica) | 30.0 |
| Kelzan ® (thickener) (Xanthan gum) | 0.5 |
| Water | 31.2 |

Preparation: The toxicant is absorbed onto the HiSil ® carrier. The Duponal ® and Reax ® are then added and the entire dry mixture blended until homogeneous. The composition is then micronized to a fine particle size. The resulting powder is suspended in water and the Kelzan ® added.

Compositions and formulations according to the present invention may also include known pesticidal compounds. This expands the spectrum of activity of the preparations and may give rise to synergism.

The following known insecticidal, fungicidal and acaricidal compounds are suitable for use in such a combined preparation.

Insecticides such as:

Chlorinated hydrocarbons, for example, 2,2-bis(p-chlorophenyl)-1,1,1-trichloroethane and hexachloroepoxyoctahydrodimethanonaphthalene;

Carbamates, for example, N-methyl-1-naphthylcarbamate;

Dinitrophenols, for example, 2-methyl-4,6-dinitrophenol and 2-(2-butyl)-4,6-dinitrophenyl-3,3-dimethylacrylate;

Organic phosphorus compounds, such as dimethyl-2-methoxy-3-carbonyl-1-methylvinyl phosphate, 0,0-diethyl-0-p-nitrophenylphosphorothioate; N-monomethylamide of 0,0-dimethyldithiophosphorylacetic acid;

Diphenylsulfides, for example, p-chlorobenzyl or p-chlorophenyl sulfide and 2,4,4',5-tetrachlorodiphenylsulfide;

Diphenylsulfonates, for example, p-chlorophenylbenzenesulfonate;

Methylcarbinols, for example, 4,4-dichloro-1-trichloromethylbenzhydrol;

Quinoxaline compounds, such as methylquinoxaline dithiocarbonate;

Amidines such as N'-(4-chloro-2-methylphenyl) N,N-dimethylformamidine;

Pyrethroids such as Allethrin;

Biologicals such as *Bacillus thuringiensis* preparations;

Organic tin compounds such as tricyclohexyltin hydroxide;

Synergists such as piperonyl butoxide.

Fungicides such as:

Organic mercury compounds, for example, phenylmercuryacetate and methylmercurycyanoguanide;

Organic tin compounds, for example, triphenyltin hydroxide and triphenyltin acetate;

Alkylenebisdithiocarbamates, for example, zinc ethylenebisthiocarbamate and manganese ethylenebisdithiocarbamate; and 2,4-dinitro-6-(2-octyl-phenylcrotonate), 1-bis(dimethylamino)phosphoryl-3-phenyl-5-amino-1,2,4-triazole, 6-methylquinoxaline-2,3-dithiocarbonate, 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-Phenyl-N'-dimethylsulfonyldiamide and tetrachloroisophthalonitrile

BIOLOGICAL ACTIVITY

It has been found by biological evaluation that compounds according to the present invention have pesticidal activity and are capable of controlling larvae and adult forms of pests, especially inserts from the order Lepidoptera. One skilled in the art will know how to determine the activity of a given compound against a given insect and the dosage required to obtain general or selective insecticidal effects. The compounds of the present invention in part affect the normal development of insects, particularly insects from the order Lepidoptera, by directly and/or indirectly influencing the moulting process.

As previously noted, the compounds of the present invention are particularly suitable for controlling plant destructive insects in crops of cultivated plants, such as, but not limited to, cotton, vegetables, corn and other cereals and the like; forestry, such as, but not limited to, birch, spruce, pine, fir and the like; and ornamental plants, flowers and trees. Compounds of the present invention are also particularly suitable for controlling insects destructive to stored commodities such as seeds and the like; fruit crops, such as, but not limited to fruit and/or citrus trees, raspberry bushes and the like; and turf, such as, but not limited to, lawns, sod and the like.

In evaluating the pesticidal activity of the compounds of this invention, the following test procedures were employed.

A test solution containing 600 parts per million (ppm) was made by dissolving the test compound in a solvent (acetone:methanol, 1:1), adding water to give an acetone:methanol:water system of 5:5:90 and then a surfactant. A 1:1 mixture of an alkylarylpolyetheralcohol (sold under the trademark Triton ® X-155) and a modified phthalic glycerol alkyl resin (sold under the trademark Triton ® B-1956) was utilized at the equivalent of 1 ounce per 100 gal. of test solution as a surfactant.

Initial evaluations were made on one or more of the following pests:

| Code Symbol | Common Name | Latin Name |
|---|---|---|
| SAW | Southern Armyworm | *Spodoptera eridania* |
| MBB | Mexican Bean Beetle | *Epilachna varivestis* |
| BW | Boll Weevil | *Anthonomus grandis grandis* |

For the foliar bean beetle and armyworm tests, individual bean (*Phaseolus limensis* var. Woods' Prolific) leaves are placed on moistened pieces of filter paper in Petri dishes. The leaves are then sprayed with the test solution using a rotating turntable and allowed to dry. The dishes are infested with 10 third instar larvae of Southern armyworm or Mexican bean beetle. The dishes are then covered.

For the Boll Weevil test ten adult weevils are placed in a 0.5 pint glass Mason jar containing a small cube of apple. The weevils are confined to the jars by fiberglass screen mesh secured by a screw-type rim cap. The jars are then sprayed with the test solution using a rotating turntable, directing the spray through the mesh into the jar.

Percent mortalities for the bean beetle and armyworm evaluations are determined 96 hours after treatment. Boll weevil mortality is determined 48 after treatment. Evaluations are based on a scale of 0–100 percent in which 0 equals no activity and 100 equals total kill.

The rotating turntable consists of a fixed, continuously operating spray nozzle under which targets are rotated at a fixed speed and distance. If the target is a Petri dish (such as for the armyworm), the distance from the nozzle is 15 inches. If the target is a Mason jar, the distance between the screened lid and the nozzle is 6 inches (10 inches from the base of the jar to the nozzle). The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and No. 70 air cap. At the 10 psig ($C_1$-$C_6$)alkoxyalkoxy having independently the stated number of carbon atoms in each alkyl group; carboxyoxy; ($C_1$-$C_6$)alkoxycarbonyloxy; ($C_2$-$C_6$)alkenyl optionally substituted with halo, cyano, ($C_1$-$C_4$)alkyl, ($C_1$-$C_4$)alkoxy, ($C_1$-$C_4$)haloalkoxy or ($C_1$-$C_4$)alkylthio; ($C_2$-$C_6$)alkenylcarbonyl; ($C_2$-$C_6$)alkadienyl; ($C_2$-$C_6$)alkynyl optionally substituted with halo, cyano, nitro, hydroxy, ($C_1$-$C_4$)alkyl, ($C_1$-$C_4$)alkoxy, ($C_1$-$C_4$)haloalkoxy or ($C_1$-$C_4$)alkylthio; carboxy; ($C_1$-$C_6$)carboxyalkyl; ($C_1$-$C_6$)alkoxycarboxyalkyl having independently the stated number of carbon atoms in each alkyl group; —COR; ($C_1$-$C_6$)haloalkylcarbonyl; ($C_1$-$C_6$)cyanoalkylcarbonyl; ($C_1$-$C_6$)nitroalkylcarbonyl; ($C_1$-$C_6$)alkoxycarbonyl; ($C_1$-$C_6$)haloalkoxycarbonyl; ($C_1$-$C_6$)alkanoyloxy; amino, ($C_1$-$C_6$)alkylamino or ($C_1$-$C_6$)dialkylamino having independently the stated number of carbon atoms in each alkyl group; amino or ($C_1$-$C_6$)alkylamino where the N of the amino or ($C_1$-$C_6$)alkylamino is substituted with hydroxy, ($C_1$-$C_4$)alkoxy or ($C_1$-$C_4$)alkylthio groups; —CONRR'; —OCONRR'; —NRCOR'; —NRCO$_2$R'; —OCONRCOR'; sulfhydryl; ($C_1$-$C_6$)alkylthio; ($C_1$-$C_6$)haloalkylthio; —NRCSR'; ($C_1$-$C_6$)alkylcarbonylthio; unsubstituted phenyl; substituted phenyl having one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; or when two adjacent position on the phenyl ring are substituted with alkoxy groups, these groups may be joined to form a 5- or 6-membered dioxolano or dioxano heterocyclic ring; or unsubstituted six-membered heterocycle or substituted six-membered heterocycle consisting of carbon and nitrogen atoms in the heterocycle ring and having one, two, three or four nitrogen atoms and two to five nuclear carbon atoms where the substituents are from one to three of the same or different halo; nitro; hydroxy; ($C_1$-$C_6$)alkyl; ($C_1$-$C_6$)alkoxy; ($C_1$-$C_6$)thioalkoxy; carboxy; ($C_1$-$C_6$)alkoxycarbonyl; ($C_1$-$C_6$)carboxyalkyl; ($C_1$-$C_6$)alkoxycarbonyl having independently the stated number of carbon atoms in each alkyl group; —CONRR'; amino, ($C_1$-$C_6$)alkylamino or ($C_1$-$C_6$)dialkylamino having independently the stated number of carbon atoms in each alkyl group; —NRCOR'; ($C_1$-$C_6$)alkylthio; unsubstituted phenyl; or substituted phenyl having one to three of the same or different halo, nitro, ($C_1$-$C_6$)alkyl, ($C_1$-$C_6$)haloalkyl, ($C_1$-$C_6$)alkoxy, ($C_1$-$C_6$)haloalkoxy, carboxy, ($C_1$-$C_4$)alkoxycarbonyl, amino, ($C_1$-$C_4$)alkylamino or ($C_1$-$C_4$)dialkylamino having independently the stated number of carbon atoms in each alkyl group;

where R and R' are hydrogen or ($C_1$-$C_6$)alkyl; and agronomically acceptable salts thereof; where one of A or B is an unsubstituted or substituted six-membered heterocycle as defined above provided that B is not 4-alkyl substituted phenyl or 3-alkoxy substituted when A is 2-pyridyl.

2. A compound having the formula

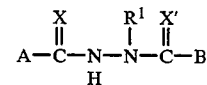

wherein

X and X' are the same or different O, S or NR;

$R^1$ is unsubstituted ($C_3$-$C_{10}$) branched alkyl or a ($C_1$-$C_4$) straight chain alkyl substituted with one or two of the same or different ($C_3$-$C_6$)cycloalkyl; and A and B are unsubstituted phenyl or substituted phenyl where the substituents are from one to five of the same or different halo; nitro; cyano; hydroxy; ($C_1$-$C_6$)alkyl; ($C_1$-$C_6$)haloalkyl; ($C_1$-$C_6$)cyanoalkyl; ($C_1$-$C_6$)alkoxy; ($C_1$-$C_6$)haloalkoxy; ($C_1$-$C_6$)alkoxyalkyl having independently the stated number of carbon atoms in each alkyl group; ($C_1$-$C_6$)alkoxyalkoxy having independently the stated number of carbon atoms in each alkyl group; carboxyoxy; ($C_1$-$C_6$)alkoxycarbonyloxy; ($C_2$-$C_6$)alkenyl optionally substituted with halo, cyano, ($C_1$-$C_4$)alkyl, ($C_1$-$C_4$)alkoxy, ($C_1$-$C_4$)haloalkoxy or ($C_1$-$C_4$)alkylthio; ($C_2$-$C_6$)alkenylcarbonyl; ($C_2$-$C_6$)alkadienyl; ($C_2$-$C_6$)alkynyl optionally substituted with halo, cyano, nitro, hydroxy, ($C_1$-$C_4$)alkyl, ($C_1$-$C_4$)alkoxy, ($C_1$-$C_4$)haloalkoxy or ($C_1$-$C_4$)alkylthio; carboxy; ($C_1$-$C_6$)carboxyalkyl; ($C_1$-$C_6$)alkoxycarboxyalkyl having independently the stated number of carbon atoms in each alkyl group; —COR; ($C_1$-$C_6$)haloalkylcarbonyl; ($C_1$-$C_6$)cyanoalkylcarbonyl; ($C_1$-$C_6$)nitroalkylcarbonyl; ($C_1$-$C_6$)alkoxycarbonyl; ($C_1$-$C_6$)haloalkoxycarbonyl; ($C_1$-$C_6$)alkanoyloxy; amino, ($C_1$-$C_6$)alkylamino or ($C_1$-$C_6$)dialkylamino having independently the stated number of carbon atoms in each alkyl group; amino or ($C_1$-$C_6$)alkylamino where the N of the amino or ($C_1$-$C_6$)alkylamino is substituted with hydroxy, ($C_1$-$C_4$)alkoxy or ($C_1$-$C_4$)alkylthio groups; —CONRR'; —OCONRR'; —NRCOR'; —NRCO$_2$R'; —OCONRCOR'; sulfhydryl; ($C_1$-$C_6$)alkylthio; ($C_1$-$C_6$)haloalkylthio; —NRCSR'; ($C_1$-$C_6$)alkylcarbonylthio; unsubstituted phenyl; substituted phenyl having one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; or when two adjacent position on the phenyl ring are substituted with alkoxy group, these groups may be joined to form a 5- or 6-membered dioxolano or dioxano heterocyclic ring; or unsubstituted six-membered heterocycle or substituted six-membered heterocycle having one nitrogen atom and five nuclear carbon atoms where the substituents are from one to three of the same or different halo; nitro; hydroxy; ($C_1$-$C_6$)alkyl; ($C_1$-$C_6$)alkoxy; ($C_1$-$C_6$)thioalkoxy; carboxy; ($C_1$-$C_6$)alkoxycarbonyl; ($C_1$-$C_6$)carboxyalkyl; ($C_1$-$C_6$)alkoxycarbonylalkyl having independently the stated number of carbon atoms in each alkyl group; —CONRR'; amino, ($C_1$-$C_6$)alkylamino; ($C_1$-$C_6$)dialkylamino having independently the stated number of carbon atoms in each alkyl group; —NRCOR'; ($C_1$-$C_6$)alkylthio; unsubstituted phenyl; or substituted phenyl having one to three of the same or different halo, nitro, ($C_1$-$C_6$)alkyl, ($C_1$-$C_6$)haloalkyl, ($C_1$-$C_6$)alkoxy, ($C_1$-$C_6$)haloalkoxy, carboxy, ($C_1$-$C_4$)alkoxycarbonyl, amino, ($C_1$-$C_4$)alkylamino or ($C_1$-$C_4$)dialkylamino having independently the stated number of carbon atoms in each alkyl group;

where R and R' are hydrogen or ($C_1$-$C_6$)alkyl; and agronomically acceptable salts thereof; where one of A or B is an unsubstituted or substituted six-membered heterocycle as defined above provided that B is not 4-alkyl substituted phenyl or 3-alkoxy substituted phenyl when A is 2-pyridyl.

3. A compound according to claim 2 wherein
X and X' are O or S;
$R^1$ is branched ($C_3$-$C_8$)alkyl; and A and B are unsubstituted phenyl or substituted phenyl having one to three of the same or different halo; nitro; cyano; ($C_1$-$C_4$)alkyl; ($C_1$-$C_4$)haloalkyl; ($C_1$-$C_4$)cyanoalkyl; ($C_1$-$C_4$)alkoxy; ($C_1$-$C_4$)alkoxyalkyl having independently the stated number of carbon atoms in each alkyl group; —COZ; ($C_1$-$C_4$)alkoxycarbonyl; ($C_1$-$C_4$)alkanoyloxy; unsubstituted phenyl; substituted phenyl having one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, or —NZZ'; or phenoxy where the phenyl ring is unsubstituted or substituted with one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy or —NZZ'; or unsubstituted six-membered heterocycle or substituted six-membered heterocycle having one nitrogen atom and 5 nuclear carbon atoms where the substituents are one to two of the same or different halo; nitro; ($C_1$-$C_4$)alkyl; ($C_1$-$C_4$)alkoxy; ($C_1$-$C_4$)thioalkoxy; —NZZ'; unsubstituted phenyl; or substituted phenyl having one or two of the same or different halo, nitro, ($C_1$-$C_4$)alkyl, ($C_1$-$C_4$)haloalkyl, ($C_1$-$C_4$)alkoxy, ($C_1$-$C_4$)haloalkoxy, carboxy, or —NZZ';

where Z and Z' are hydrogen or ($C_1$-$C_4$)alkyl; and agronomically acceptable salts thereof, where one of A or B is an unsubstituted or substituted six-membered heterocycle as defined.

4. The compound according to claim 3 wherein
X and X' are O;
$R^1$ is branched ($C_4$-$C_7$)alkyl; and
A and B are unsubstituted phenyl or substituted phenyl where the substituents are from one to three of the same or different halo, nitro, ($C_1$-$C_4$)alkyl, ($C_1$-$C_4$)alkoxy, or ($C_1$-$C_4$)haloalkyl; or unsubstituted six-membered heterocycle or substituted six-membered heterocycle having one nitrogen atom and five nuclear carbon atoms where the substituents are one or two of the same or different, halo, nitro, ($C_1$-$C_4$)alkyl, ($C_1$-$C_4$)alkoxy or ($C_1$-$C_4$)thioalkoxy; and agronomically acceptable salts thereof, where one of A or B is an unsubstituted or substituted six-membered heterocycle as defined above.

5. The compound according to claim 4 wherein
X and X' are O;
$R^1$ is t-butyl, neopentyl (2,2-dimethylpropyl) or 1,2,2-trimethylpropyl; and A and B are unsubstituted phenyl or substituted phenyl where the substituent is one or two of the same or different chloro, fluoro, bromo, iodo, nitro, methyl, ethyl or trifluoromethyl; or unsubstituted pyridyl or substituted pyridyl where the substituent is halo, nitro, ($C_1$-$C_4$)alkyl, ($C_1$-$C_4$)alkoxy or ($C_1$-$C_4$)thioalkoxy; and agronomically acceptable salts thereof, where one of A or B is an unsubstituted or substituted six-membered heterocycle as defined above.

6. The compound according to claim 5 wherein
X and X' are O;
$R^1$ is t-butyl; and
A and B are unsubstituted phenyl or substituted phenyl where the substituents are one or two of the same or different chloro, fluoro, bromo, iodo, nitro, methyl, ethyl or trifluoromethyl; unsubstituted pyridyl or pyridyl substituted with halo, $(C_1-C_3)$alkyl or thiomethoxy; and agronomically acceptable salts thereof, where one of A or B is an unsubstituted or substituted six-membered heterocycle as defined above.

7. The compound according to claim 6 wherein

X and X' are O;

$R^1$ is t-butyl; and

A is 2-pyridyl and B is selected from the group consisting of phenyl, 3-methylphenyl, 4-fluorophenyl and 2-chloro, 4-fluorophenyl;

A is 5-bromo-3-pyridyl and B is 4-chlorophenyl;

A is 2-chloro-3-pyridyl and B is 3-methylphenyl; or

A is 2,3-dimethylphenyl and B is 2-chloro-3-pyridyl.

8. An insecticidal composition comprising an agronomically acceptable carrier and an insecticidally effective amount of the compound of claim 1.

9. An insecticidal composition comprising an agronomically acceptable carrier and an insecticidally effective amount of the compound of claim 6.

10. The composition according to claim 8 wherein said compound is present at from about 0.0001 to about 99% by weight of the composition.

11. The composition according to claim 10 wherein said compound is present at from about 0.001 to about 90% by weight of the composition.

12. The composition according to claim 11 wherein said compound is present at from about 0.01 to about 75% by weight of the composition.

13. The composition according to claim 9 wherein said compound is selected from the group consisting of N'-t-butyl-N-(2-pyridylcarbonyl)-N'-benzoylhydrazine, N'-t-butyl-N-(2-pyridylcarbonyl)-N'-(3-methylbenzoyl)hydrazine, N'-t-butyl-N-(5-bromonicotinoyl)-N'-(4-chlorobenzoyl)hydrazine, N'-t-butyl-N-(2-pyridylcarbonyl)-N'-(4-fluorobenzoyl)hydrazine, N'-t-butyl-N-(2-chloro-3-pyridylcarbonyl)-N'-(3-methylbenzoyl)hydrazine, N'-t-butyl-N-(2,3-dimethylbenzoyl)-N'-(2-chloro-3-pyridylcarbonyl)hydrazine and N'-t-butyl-N-(2-pyridylcarbonyl)-N'-(2-chloro,4-fluorobenzoyl)hydrazine.

14. A method of controlling insects which comprises contacting said insects with the insecticidal compound according to claim 1.

15. A method of controlling insects which comprises contacting said insects with the insecticidal compound according to claim 6.

16. The method of claim 12 wherein said composition is applied at from about 10 grams to about 10 kilograms per hectare of the compound.

17. The method of claim 16 wherein said composition is applied at from about 100 grams to about 5 kilograms per hectare of the compound.

18. The method of claim 15 wherein said composition is applied at from about 10 grams to about 10 kilograms per hectare of the compound.

19. The method of claim 18 wherein said composition is applied at from about 100 grams to about 5 kilograms per hectare of the compound.

20. The method of claim 14 wherein said insects are from the order Lepidoptera.

21. The method of claim 15 wherein said insects are from the order Lepidoptera.

22. The compound according to claim 1 wherein

X and X' are O or S;

$R^1$ is branched $(C_3-C_8)$alkyl; and

A and B are unsubstituted phenyl or substituted phenyl having one to three of the same or different halo; nitro; cyano; $(C_1-C_4)$alkyl; $(C_1-C_4)$haloalkyl; $(C_1-C_4)$cyanoalkyl; $(C_1-C_4)$alkoxy; $(C_1-C_4)$alkoxyalkyl having independently the stated number of carbon atoms in each alkyl group; —COZ; $(C_1-C_4)$alkoxycarbonyl; $(C_1-C_4)$alkanoyloxy; unsubstituted phenyl; substituted phenyl having one or two of the same or different halo, nitro, $(C_1-C_4)$alkyl, $(C_1-C_4)$alkoxy, carboxy, $(C_1-C_4)$alkoxycarbonyl, $(C_1-C_4)$alkanoyloxy or —NZZ'; or phenoxy where the phenyl ring is unsubstituted or substituted with one or two of the same or different halo, nitro, $(C_1-C_4)$alkyl, $(C_1-C_4)$alkoxy, carboxy, $(C_1-C_4)$alkoxycarbonyl, $(C_1-C_4)$alkanoyloxy or —NZZ'; or unsubstituted six-membered heterocycle or substituted six-membered heterocycle having two nitrogen atoms and 4 nuclear carbon atoms where the substituents can be one or two of the same or different halo; nitro; $(C_1-C_4)$alkyl; $(C_1-C_4)$alkoxy; $(C_1-C_4)$thioalkoxy; —NZZ'; unsubstituted phenyl; or substituted phenyl having one or two of the same or different halo, nitro, $(C_1-C_4)$alkyl, $(C_1-C_4)$haloalkyl, $(C_1-C_4)$alkoxy, $(C_1-C_4)$haloalkoxy, carboxy, or —NZZ';

where Z and Z' are hydrogen or $(C_1-C_4)$alkyl; and agronomically acceptable salts thereof, where one of A or B is an unsubstituted or substituted six-membered heterocycle as defined.

23. The compound according to claim 22 wherein

X and X' are O;

$R^1$ is branched $(C_4-C_7)$alkyl; and

A and B are unsubstituted phenyl or substituted phenyl where the substituents can be from one to three of the same or different halo, nitro, $(C_1-C_4)$alkyl, $(C_1-C_4)$alkoxy, or $(C_1-C_4)$haloalkyl; or unsubstituted six-membered heterocycle or substituted six-membered heterocycle having two nitrogen atoms and five nuclear carbon atoms where the substituents can be one or two of the same or different, halo, nitro, $(C_1-C_4)$alkyl, $(C_1-C_4)$alkoxy or $(C_1-C_4)$thioalkoxy; and agronomically acceptable salts thereof, where one of A or B is an unsubstituted or substituted six-membered heterocycle as defined above.

24. The compound according to claim 23 wherein

X and X' are O;

$R^1$ is t-butyl, neopentyl or 1,2,2-trimethylpropyl; and

A and B are unsubstituted phenyl or substituted phenyl where the substituents can be one or two of the same or different chloro, fluoro, bromo, iodo, nitro, methyl, ethyl, methoxy or trifluoromethyl; or unsubstituted 1,3- or 1,4-diazinyl or substituted 1,3- or 1,4-diazinyl where the substituent can be halo, nitro, $(C_1-C_4)$alkyl or $(C_1-C_4)$alkoxy; and agronomically acceptable salts thereof, where one of A or B is an unsubstituted or substituted six-membered heterocycle as defined above.

25. The compound according to claim 24 wherein

X and X' are O;

$R^1$ is t-butyl; and

A and B are unsubstituted phenyl or substituted phenyl where the substituents can be one or two of the same or different chloro, fluoro, bromo, iodo, nitro, methyl, ethyl or trifluoromethyl; or 1,3- or 1,4-diazinyl; and agronomically acceptable salts thereof, where one of A or B is an unsubstituted or substituted six-membered heterocycle as defined above.

26. An insecticidal composition comprising an agronomically acceptable carrier and an insecticidally effective amount of the compound of claim 25.

27. A method of controlling insects which comprises contacting said insects with the insecticidal composition according to claim 25.

28. The method of claim 27 wherein said composition is applied at from about 10 grams to about 10 kilograms per hectare of the compound.

29. The method of claim 28 wherein said composition is applied at from about 100 grams to about 5 kilograms per hectare of the compound.

30. The method of claim 27 wherein said insects are from the order Lepidoptera.

31. An insecticidal composition comprising an agronomically acceptable carrier and an insecticidally effective amount of the compound of claim 2.

32. An insecticidal composition comprising an agronomically acceptable carrier and an insecticidally effective amount of the compound of claim 3.

33. An insecticidal composition comprising an agronomically acceptable carrier and an insecticidally effective amount of the compound of claim 4.

34. An insecticidal composition comprising an agronomically acceptable carrier and an insecticidally effective amount of the compound of claim 5.

35. The composition according to claim 31 wherein said compound is present at from about 0.0001 to about 99% by weight of the composition.

36. The composition according to claim 9 wherein said compound is present at from about 0.0001 to about 99% by weight of the composition.

37. The composition according to claim 35 wherein said compound is present at from about 0.001 to about 90% by weight of the composition.

38. The composition according to claim 36 wherein said compound is present at from about 0.001 to about 90% by weight of the composition.

39. The composition according to claim 37 wherein said compound is present at from about 0.01 to about 75% by weight of the composition.

40. The composition according to claim 38 wherein said compound is present at from about 0.01 to about 75% by weight of the composition.

41. The composition according to claim 40 wherein said agronomically acceptable carrier is a liquid.

42. The composition according to claim 41 additionally containing an emulsifying agent, said composition being in the form of an emulsifiable concentrate.

43. The composition according to claim 40 wherein said agronomically acceptable carrier is a solid.

44. The composition according to claim 43 additionally containing a dispersing agent, said composition being in the form of a wettable powder.

45. The composition according to claim 43 additionally containing liquid agronomically acceptable carrier and a dispersing agent, said composition being in the form of a flowable.

46. The composition according to claim 43 wherein said composition is in the form of a dust.

47. The composition according to claim 43 wherein additionally containing a binding agent, said composition being in the form of a granule.

48. The composition according to claim 43 wherein additionally containing an attractant agent, said composition being in the form of a bait.

49. An insecticidal composition comprising an agronomically acceptable carrier and an insecticidally effective amount of the compound of claim 21.

50. An insecticidal composition comprising an agronomically acceptable carrier and an insecticidally effective amount of the compound of claim 22.

51. An insecticidal composition comprising an agronomically acceptable carrier and an insecticidally effective amount of the compound of claim 23.

52. The composition according to claim 51 wherein said compound is present at from about 0.0001 to about 99% by weight of the composition.

53. The composition according to claim 52 wherein said compound is present at from about 0.001 to about 90% by weight of the composition.

54. The composition according to claim 53 wherein said compound is present at from about 0.01 to about 75% by weight of the composition.

55. A method of controlling insects which comprises contacting said insects with the composition according to claim 2.

56. A method of controlling insects which comprises contacting said insects with the composition according to claim 3.

57. A method of controlling insects which comprises contacting said insects with the composition according to claim 4.

58. A method of controlling insects which comprises contacting said insects with the composition according to claim 5.

59. The method of claim 55 wherein said composition is applied at from about 10 grams to about 15 kilograms per hectare of the compound.

60. The method of claim 58 wherein said composition is applied at from about 10 grams to about 10 kilograms per hectare of the compound.

61. The method of claim 59 wherein said composition is applied at from about 100 grams to about 5 kilograms per hectare of the compound.

62. The method of claim 60 wherein said composition is applied at from about 100 grams to about 5 kilograms per hectare of the compound.

63. A method of controlling insects which comprises contacting said insects with the composition according to claim 21.

64. A method of controlling insects which comprises contacting said insects with the composition according to claim 22.

65. A method of controlling insects which comprises contacting said insects with the composition according to claim 23.

66. The method of claim 26 wherein said insects are from the order Lepidoptera.

67. The method of claim 55 wherein said insects are from the order Lepidoptera.

68. The method of claim 14 wherein the compound is applied foliarly.

69. The method of claim 15 wherein the compound is applied foliarly.

70. The method of claim 26 wherein the compound is applied foliarly.

71. The method of claim 55 wherein the compound is applied foliarly.

72. A compound having the formula

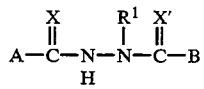

wherein

X and X' are the same or different O, S or NR;

$R^1$ is unsubstituted ($C_3$-$C_{10}$) branched alkyl or a ($C_1$-$C_4$) straight chain alkyl substituted with one or two of the same or different ($C_3$-$C_6$)cycloalkyl; and A and B are unsubstituted phenyl or substituted phenyl where the substituents are from one to five of the same or different halo; nitro; cyano; hydroxy; ($C_1$-$C_6$)alkyl; ($C_1$-$C_6$)haloalkyl; ($C_1$-$C_6$)cyanoalkyl; ($C_1$-$C_6$)alkoxy; ($C_1$-$C_6$)haloalkoxy; ($C_1$-$C_6$)alkoxyalkyl having independently the stated number of carbon atoms in each alkyl group; ($C_1$-$C_6$)alkoxyalkoxy having independently the stated number of carbon atoms in each alkyl group; carboxyoxy; ($C_1$-$C_6$)alkoxycarbonyloxy; ($C_2$-$C_6$)alkenyl optionally substituted with halo, cyano, ($C_1$-$C_4$)alkyl, ($C_1$-$C_4$)alkoxy, ($C_1$-$C_4$)haloalkoxy or ($C_1$-$C_4$)alkylthio; ($C_2$-$C_6$)alkenylcarbonyl; ($C_2$-$C_6$)alkadienyl; ($C_2$-$C_6$)alkynyl optionally substituted with halo, cyano, nitro, hydroxy, ($C_1$-$C_4$)alkyl, ($C_1$-$C_4$)alkoxy, ($C_1$-$C_4$)haloalkoxy or ($C_1$-$C_4$)alkylthio; carboxy; ($C_1$-$C_6$)carboxyalkyl; ($C_1$-$C_6$)alkoxycarboxyalkyl having independently the stated number of carbon atoms in each alkyl group; —COR; ($C_1$-$C_6$)haloalkylcarbonyl; ($C_1$-$C_6$)cyanoalkylcarbonyl; ($C_1$-$C_6$)nitroalkylcarbonyl; ($C_1$-$C_6$)alkoxycarbonyl; ($C_1$-$C_6$)haloalkoxycarbonyl; ($C_1$-$C_6$)alkanoyloxy; amino, ($C_1$-$C_6$)alkylamino or ($C_1$-$C_6$)dialkylamino having independently the stated number of carbon atoms in each alkyl group; amino or ($C_1$-$C_6$)alkylamino where the N of the amino or ($C_1$-$C_6$)alkylamino is substituted with hydroxy, ($C_1$-$C_4$)alkoxy or ($C_1$-$C_4$)alkylthio groups; —CONRR'; —OCONRR'; —NRCOR'; —NRCO$_2$R'; —OCONRCOR'; sulfhydryl; ($C_1$-$C_6$)alkylthio; ($C_1$-$C_6$)haloalkylthio; —NRCSR'; ($C_1$-$C_6$)alkylcarbonylthio; unsubstituted phenyl; substituted phenyl having one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; or when two adjacent position on the phenyl ring are substituted with alkoxy groups, these groups may be joined to form a 5- or 6-membered dioxolano or dioxano heterocyclic ring; or unsubstituted six-membered heterocycle or substituted six-membered aromatic heterocycle consisting of carbon and nitrogen atoms in the heterocycle ring and having one, two, three or four nitrogen atoms and two to five nuclear carbon atoms where the substituents are from one to three of the same or different halo; nitro; hydroxy; ($C_1$-$C_6$)alkyl; ($C_1$-$C_6$)alkoxy; ($C_1$-$C_6$)thioalkoxy; carboxy; ($C_1$-$C_6$)alkoxycarbonyl; ($C_1$-$C_6$)carboxyalkyl; ($C_1$-$C_6$)alkoxycarbonyl having independently the stated number of carbon atoms in each alkyl group; —CONRR'; amino, ($C_1$-$C_6$)alkylamino or ($C_1$-$C_6$)dialkylamino having independently the stated number of carbon atoms in each alkyl group; —NRCOR'; ($C_1$-$C_6$)alkylthio; unsubstituted phenyl; or substituted phenyl having one to three of the same or different halo, nitro, ($C_1$-$C_6$)alkyl, ($C_1$-$C_6$)haloalkyl, ($C_1$-$C_6$)alkoxy, ($C_1$-$C_6$)haloalkoxy, carboxy, ($C_1$-$C_4$)alkoxycarbonyl, amino, ($C_1$-$C_4$)alkylamino or ($C_1$-$C_4$)dialkylamino having independently the stated number of carbon atoms in each alkyl group;

where R and R' are hydrogen or ($C_1$-$C_6$)alkyl; and agronomically acceptable salts thereof; where one of A or B is an unsubstituted or substituted six-membered heterocycle as defined above provided that B is not 4-alkyl substituted phenyl or 3-alkoxy substituted when A is 2-pyridyl.

73. A compound having the formula

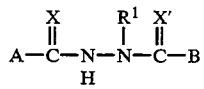

wherein

X and X' are the same or different O, S or NR;

$R^1$ is unsubstituted ($C_3$-$C_{10}$) branched alkyl or a ($C_1$-$C_4$) straight chain alkyl substituted with one or two of the same or different ($C_3$-$C_6$)cycloalkyl; and A and B are unsubstituted phenyl or substituted phenyl where the substituents are from one to five of the same or different halo; nitro; cyano; hydroxy; ($C_1$-$C_6$)alkyl; ($C_1$-$C_6$)haloalkyl; ($C_1$-$C_6$)cyanoalkyl; ($C_1$-$C_6$)alkoxy; ($C_1$-$C_6$)haloalkoxy; ($C_1$-$C_6$)alkoxyalkyl having independently the stated number of carbon atoms in each alkyl group; ($C_1$-$C_6$)alkoxyalkoxy having independently the stated number of carbon atoms in each alkyl group; carboxyoxy; ($C_1$-$C_6$)alkoxycarbonyloxy; ($C_2$-$C_6$)alkenyl optionally substituted with halo, cyano, ($C_1$-$C_4$)alkyl, ($C_1$-$C_4$)alkoxy, ($C_1$-$C_4$)haloalkoxy or ($C_1$–$C_4$)alkylthio; ($C_2$–$C_6$)alkenylcarbonyl; ($C_2$–$C_6$)alkadienyl; ($C_2$–$C_6$)alkynyl optionally substituted with halo, cyano, nitro, hydroxy, ($C_1$–$C_4$)alkyl, ($C_1$–$C_4$)alkoxy, ($C_1$–$C_4$)haloalkoxy or ($C_1$–$C_4$)alkylthio; carboxy; ($C_1$–$C_6$)carboxyalkyl; ($C_1$–$C_6$)alkoxycarboxyalkyl having independently the stated number of carbon atoms in each alkyl group; —COR; ($C_1$–$C_6$)haloalkylcarbonyl; ($C_1$–$C_6$)cyanoalkylcarbonyl; ($C_1$–$C_6$)nitroalkylcarbonyl; ($C_1$–$C_6$)alkoxycarbonyl; ($C_1$–$C_6$)haloalkoxycarbonyl; ($C_1$–$C_6$)alkanoyloxy; amino, ($C_1$–$C_6$)alkylamino or ($C_1$–$C_6$)dialkylamino having independently the stated number of carbon atoms in each alkyl group; amino or ($C_1$–$C_6$)alkylamino where the N of the amino or ($C_1$–$C_6$)alkylamino is substituted with hydroxy, ($C_1$–$C_4$)alkoxy or ($C_1$–$C_4$)alkylthio groups; —CONRR'; —OCONRR'; —NRCOR'; —NRCO$_2$R'; —OCONRCOR'; sulfhydryl; ($C_1$–$C_6$)alkylthio; ($C_1$–$C_6$)haloalkylthio; —NRCSR'; ($C_1$–$C_6$)alkylcarbonylthio; unsubstituted phenyl; substituted phenyl having one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino ($C_1$–$C_4$)alkylamino or ($C_1$–$C_4$)dialkylamino having independently the stated number of carbon atoms in each alkyl group; phenoxy where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino ($C_1$–$C_4$)alkylamino or ($C_1$–$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; or when two adjacent position on the phenyl ring are substituted with alkoxy groups, these groups may be joined to form a 5- or 6-membered dioxolano or dioxano heterocyclic ring; or unsubstituted six-membered aromatic heterocycle or substituted six-membered atomic heterocycle having one nitrogen atom and five nuclear carbon atoms where the substituents can be from one to three of the same or different halo; nitro; hydroxy; ($C_1$–$C_6$)alkyl; ($C_1$–$C_6$)alkoxy; ($C_1$–$C_6$)thioalkoxy; carboxy; ($C_1$–$C_6$)alkoxycarbonyl; ($C_1$–$C_6$)carboxyalkyl; ($C_1$–$C_6$)alkoxycarbonylalkyl having independently the stated number of carbon atoms in each alkyl group; —CONRR'; amino, ($C_1$–$C_6$)alkylamino or ($C_1$–$C_6$)dialkylamino having independently the stated number of carbon atoms in each alkyl group; —NRCOR'; ($C_1$–$C_6$)alkylthio; unsubstituted phenyl; or substituted phenyl having one to three of the same or different halo, nitro, ($C_1$–$C_6$)alkyl, ($C_1$–$C_6$)haloalkyl, ($C_1$–$C_6$)alkoxy, ($C_1$–$C_6$)haloalkoxy, carboxy, ($C_1$–$C_4$)alkoxycarbonyl, amino, ($C_1$–$C_4$)alkylamino or ($C_1$–$C_4$)dialkylamino having independently the stated number of carbon atoms in each alkyl group;

where R and R' are hydrogen or ($C_1$–$C_6$)alkyl; and agronomically acceptable salts thereof; where one of A or B is an unsubstituted or substituted six-membered heterocycle as defined above; provided that B is not 4-alkyl substituted phenyl or 3-alkoxy substituted when A is 2-pyridyl.

74. A compound according to claim 73 wherein
X and X' are O or S;
$R^1$ is branched ($C_3$–$C_8$)alkyl; and
A and B are unsubstituted phenyl or substituted phenyl having one to three of the same or different halo; nitro; cyano; ($C_1$–$C_4$)alkyl; ($C_1$–$C_4$)haloalkyl; ($C_1$–$C_4$)cyanoalkyl; ($C_1$–$C_4$)alkoxy; ($C_1$–$C_4$)alkoxyalkyl having independently the stated number of carbon atoms in each alkyl group; —COZ; ($C_1$–$C_4$)alkoxycarbonyl; ($C_1$–$C_4$)alkanoyloxy; unsubstituted phenyl; substituted phenyl having one or two of the same or different halo, nitro, ($C_1$–$C_4$)alkyl, ($C_1$–$C_4$)alkoxy, carboxy, ($C_1$–$C_4$)alkoxycarbonyl, ($C_1$–$C_4$)alkanoyloxy or —NZZ'; or phenoxy where the phenyl ring is unsubstituted or substituted with one or two of the same or different halo, nitro, ($C_1$–$C_4$)alkyl, ($C_1$–$C_4$)alkoxy, carboxy, ($C_1$–$C_4$)alkoxycarbonyl, ($C_1$–$C_4$)alkanoyloxy or —NZZ'; or unsubstituted six-membered aromatic heterocycle or substituted six-membered aromatic heterocycle having one nitrogen atom and 5 nuclear carbon atoms where the substituents are one to two of the same or different halo; nitro; ($C_1$–$C_4$)alkyl; ($C_1$–$C_4$)alkoxy; ($C_1$–$C_4$)thioalkoxy; —NZZ'; unsubstituted phenyl; or substituted phenyl having one or two of the same or different halo, nitro, ($C_1$–$C_4$)alkyl, ($C_1$–$C_4$)haloalkyl, ($C_1$–$C_4$)alkoxy, ($C_1$–$C_4$)haloalkoxy, carboxy, or —NZZ';

where Z and Z' are hydrogen or ($C_1$–$C_4$)alkyl; and agronomically acceptable salts thereof, where one of A or B is an unsubstituted or substituted six-membered heterocycle as defined.

75. An insecticidal composition comprising an agronomically acceptable carrier and an insecticidally effective amount of the compound of claim 72.

76. A method of controlling insects which comprises contacting said insects with the composition according to claim 75.

77. An insecticidal composition comprising an agronomically acceptable carrier and an insecticidally effective amount of the compound of claim 73.

78. A method of controlling insects which comprises contacting said insects with the composition according to claim 77.

\* \* \* \* \*